United States Patent [19]

Segev

[11] Patent Number: 6,004,826
[45] Date of Patent: Dec. 21, 1999

[54] REPAIR-MEDIATED PROCESS FOR AMPLIFYING AND DETECTING NUCLEIC ACID SEQUENCES

[75] Inventor: David Segev, Moshav Bne-Rem 40, D. N. Evtah, Israel, 79840

[73] Assignee: David Segev

[21] Appl. No.: 08/155,938

[22] Filed: Oct. 27, 1993

Related U.S. Application Data

[63] Continuation of application No. 07/841,649, Feb. 20, 1992, abandoned, which is a continuation-in-part of application No. 07/784,749, Oct. 28, 1991, abandoned, which is a continuation of application No. 07/221,750, Jul. 20, 1988, abandoned.

[51] Int. Cl.⁶ .............................. C12Q 1/68; C12P 19/34
[52] U.S. Cl. ........................... 438/6; 435/91.2; 435/91.52
[58] Field of Search ............................ 435/6, 91.2, 91.52

[56] References Cited

U.S. PATENT DOCUMENTS 4,800,159  1/1989  Mullis et al. ........................ 435/91.2

FOREIGN PATENT DOCUMENTS

| | | |
|---|---|---|
| 0246864 | 11/1987 | European Pat. Off. . |
| 320308 | 6/1989 | European Pat. Off. . |
| 324616 | 7/1989 | European Pat. Off. . |
| WO8909835 | 10/1989 | WIPO . |
| WO8912696 | 12/1989 | WIPO . |

OTHER PUBLICATIONS

Takahashi et al., Journal of Biological Chemistry 259 (16) 10,041–10,047 (1984).

*Primary Examiner*—Lisa B. Arthur
*Attorney, Agent, or Firm*—Irving N. Feit; Hoffmann & Baron, LLP

[57] ABSTRACT

This invention relates to a process for amplifying and detecting any desired specific nucleic acid sequence that exists in a nucleic acid or mixture thereof. The process comprises treating single strand RNA or separated complementary strands of DNA target with a molar excess of oligonucleotide complement pairs in which these oligonucleotide complement pairs have sequences complementary to the target, under hybridizing conditions. In one embodiment, the oligonucleotide complement pairs may have a gap of one or more bases which may be repaired (filled) by enzymes. The oligonucleotide complement pairs are joined together, forming joined, oligonucleotide product. The target/joined product hybrid nucleic acids are then denatured to single strands again, at which point both the target and the joined products can form hybrids with new oligonucleotide complement pairs. The steps of the reaction may be carried out stepwise or simultaneously and can be repeated as often as desired.

15 Claims, 4 Drawing Sheets

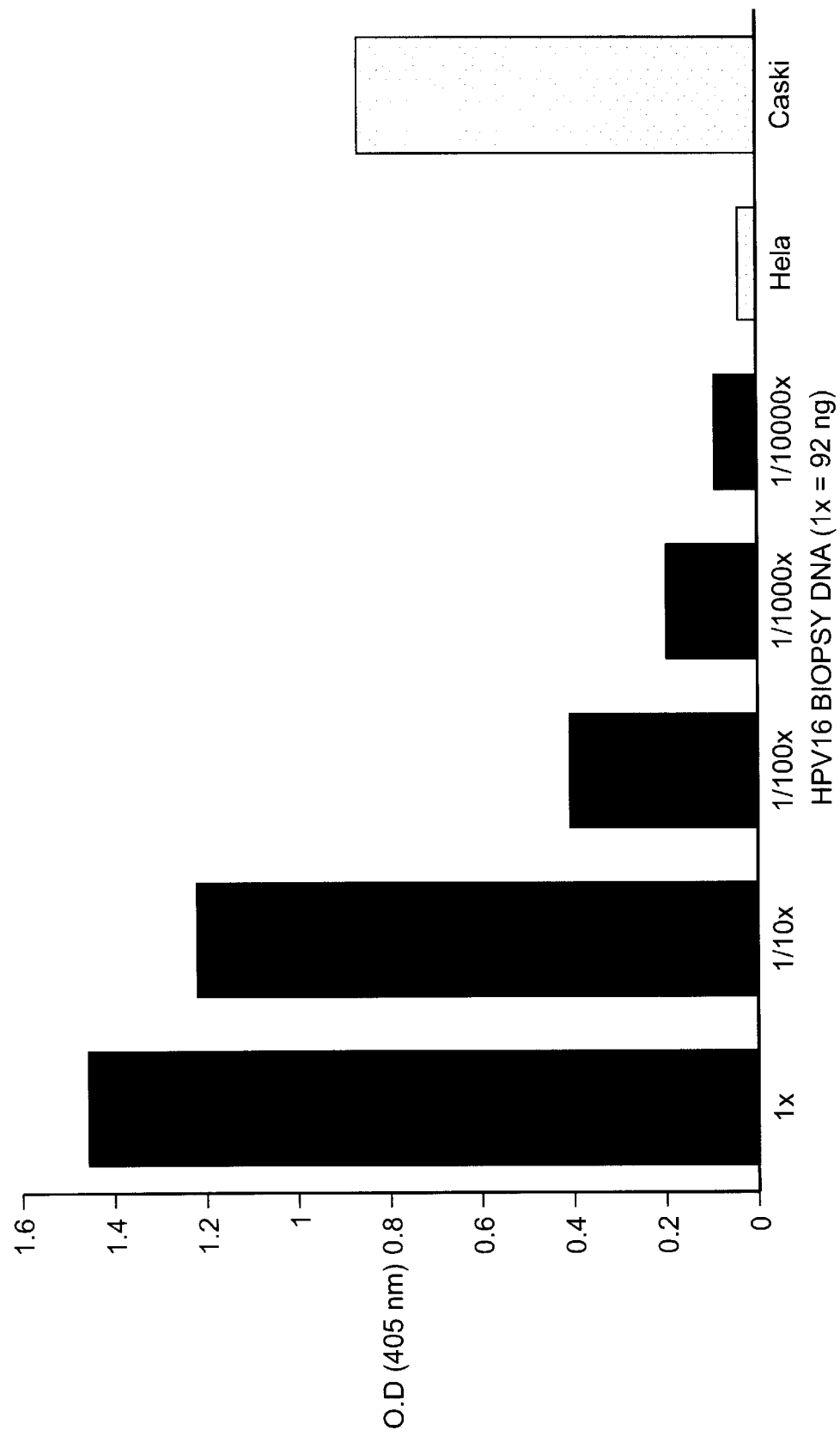

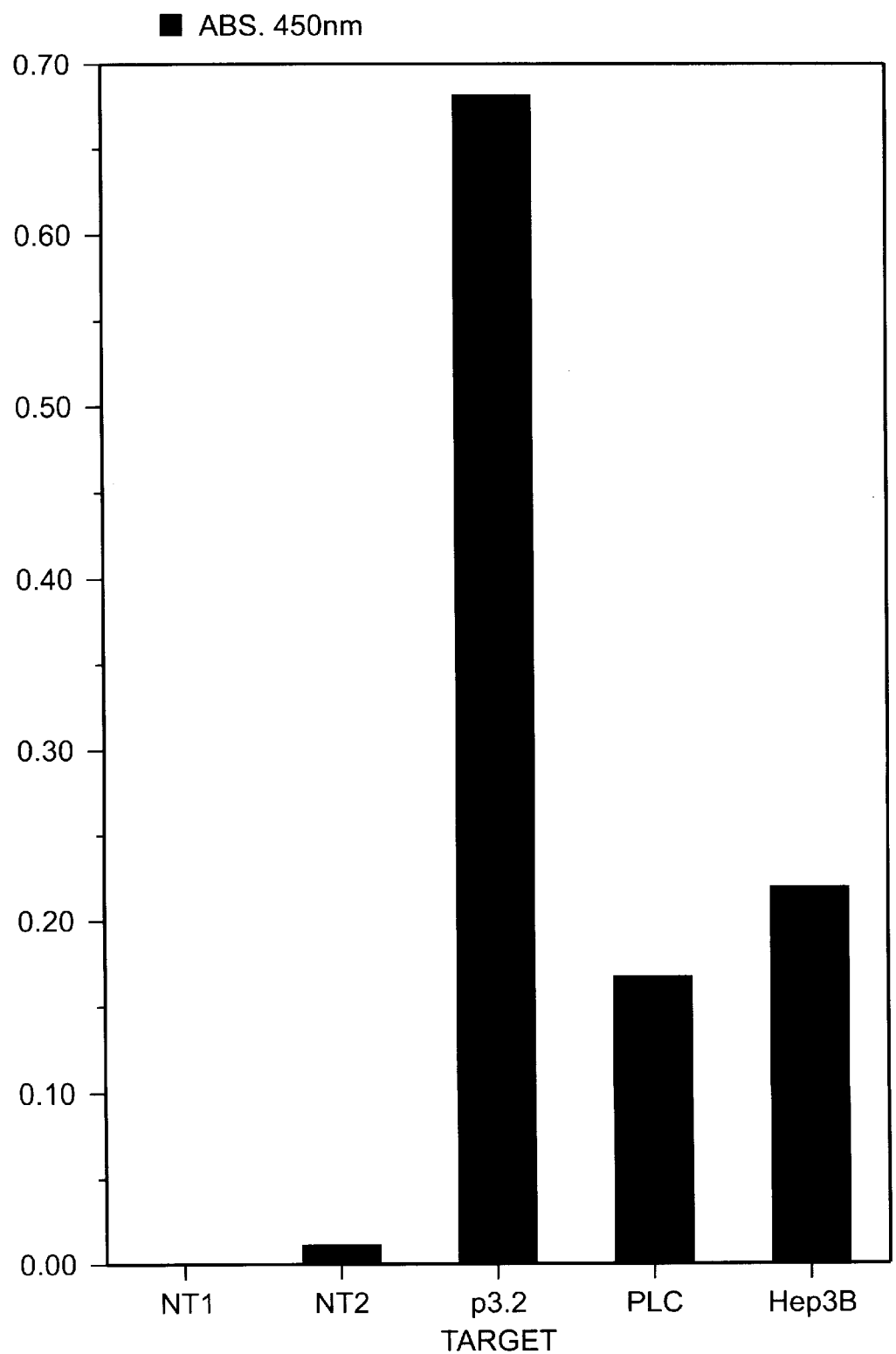
FIG-4 HBV/RCR CAPTURE ASSAY

```
                            SEQUENCE LISTING (1) GENERAL INFORMATION:

(iii) NUMBER OF SEQUENCES: 42

(2) INFORMATION FOR SEQ ID NO:1:

(i) SEQUENCE CHARACTERISTICS:
         (A) LENGTH: 47 base pairs
         (B) TYPE: nucleic acid
         (C) STRANDEDNESS: double
         (D) TOPOLOGY: linear (ii) MOLECULE TYPE: DNA (genomic)

(vi) ORIGINAL SOURCE:
         (A) ORGANISM: Human immunodeficiency virus (xi) SEQUENCE DESCRIPTION: SEQ ID NO:1:

TCCTACAAGG GAAGGCCAGG GAATTTTCTT CAGAGCAGAC CAGAGCC                47

(2) INFORMATION FOR SEQ ID NO:2:

(i) SEQUENCE CHARACTERISTICS:
         (A) LENGTH: 47 base pairs
         (B) TYPE: nucleic acid
         (C) STRANDEDNESS: double
         (D) TOPOLOGY: linear (ii) MOLECULE TYPE: DNA (genomic)

(vi) ORIGINAL SOURCE:
         (A) ORGANISM: Human immunodeficiency virus (xi) SEQUENCE DESCRIPTION: SEQ ID NO:2:

TGGCTCTGGT CTGCTCTGAA GAAAATTCCC TGGCCTTCCC TTGTAGG                47

(2) INFORMATION FOR SEQ ID NO:3:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:3:

TCCTACAAGG GAAGGCCAGG G                                            21

(2) INFORMATION FOR SEQ ID NO:4:
```

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:4:

TCCCTGGCCT TCCCTTGTAG G                                              21

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

TCTTCAGAGC AGACCAGAGC C                                              21

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

TGGCTCTGGT CTGCTCTGAA G                                              21

(2) INFORMATION FOR SEQ ID NO:7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

TCCTACAAGG GAAGGCCAGG GA                                             22

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

ATTCCCTGGC CTTCCCTTGT AGG                                            23

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single (D) TOPOLOGY: linear (ii) MOLECULE TYPE: DNA (genomic)

(xi) SEQUENCE DESCRIPTION: SEQ ID NO:9:

TCTTCAGAGC AGACCAGAGC C                                              21

(2) INFORMATION FOR SEQ ID NO:10:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:10:

TGGCTCTGGT CTGCTCTGAA G                                              21

(2) INFORMATION FOR SEQ ID NO:11:

(i) SEQUENCE CHARACTERISTICS:
            (A) LENGTH: 51 base pairs
            (B) TYPE: nucleic acid
            (C) STRANDEDNESS: double
            (D) TOPOLOGY: linear (ii) MOLECULE TYPE: DNA (genomic)

(vi) ORIGINAL SOURCE:
            (A) ORGANISM: Human immunodeficiency virus (xi) SEQUENCE DESCRIPTION: SEQ ID NO:11:

CACTTTGGAA AGGACCAGCA AAGCTCCTCT GGAAAGGTGA AGGGGCAGTA G              51

(2) INFORMATION FOR SEQ ID NO:12:

(i) SEQUENCE CHARACTERISTICS:
            (A) LENGTH: 51 base pairs
            (B) TYPE: nucleic acid
            (C) STRANDEDNESS: double
            (D) TOPOLOGY: linear (ii) MOLECULE TYPE: DNA (genomic)

(vi) ORIGINAL SOURCE:
            (A) ORGANISM: Human immunodeficiency virus (xi) SEQUENCE DESCRIPTION: SEQ ID NO:12:

CTACTGCCCC TTCACCTTTC CAGAGGAGCT TTGCTGGTCC TTTCCAAAGT G              51

(2) INFORMATION FOR SEQ ID NO:13:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:13:

GAGCTTTGCT GGTCCTTTCC AAAGTG                                         26

(2) INFORMATION FOR SEQ ID NO:14:

(i) SEQUENCE CHARACTERISTICS:
            (A) LENGTH: 26 base pairs
            (B) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO:14:

CACTTTGGAA AGGACCAGCA AAGCTC                                       26

(2) INFORMATION FOR SEQ ID NO:15:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

CTACTGCCCC TTCACCTTTC CAGAG                                        25

(2) INFORMATION FOR SEQ ID NO:16:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

CTCTGGAAAG GTGAAGGGGC AGTAG                                        25

(2) INFORMATION FOR SEQ ID NO:17:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

GAGCTTTGCT GGTCCTTTCC AAAGTG                                       26

(2) INFORMATION FOR SEQ ID NO:18:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

CACTTTGGAA AGGACCAGCA AAGCTC                                       26

(2) INFORMATION FOR SEQ ID NO:19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

CTACTGCCCC TTCACCTTTC CAGAG                                              25

(2) INFORMATION FOR SEQ ID NO:20:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

CTCTGGAAAG GTGAAGGGGC AGTAG                                              25

(2) INFORMATION FOR SEQ ID NO:21:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Chlamydia trachomatis (xi) SEQUENCE DESCRIPTION: SEQ ID NO:21:

GTCTACCACC AAGAGTTGCA AA                                                 22

(2) INFORMATION FOR SEQ ID NO:22:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Chlamydia trachomatis (xi) SEQUENCE DESCRIPTION: SEQ ID NO:22:

TTTGCAACTC TTGGTGGTAG AC                                                 22

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

AGTCTACCAC CAAGAGTTGC                                                    20

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

TGCAACTCTT GGTGGTAGAC                                                  20

(2) INFORMATION FOR SEQ ID NO:25:

(i) SEQUENCE CHARACTERISTICS:
          (A) LENGTH: 50 base pairs
          (B) TYPE: nucleic acid
          (C) STRANDEDNESS: double
          (D) TOPOLOGY: linear (ii) MOLECULE TYPE: DNA (genomic)

(vi) ORIGINAL SOURCE:
          (A) ORGANISM: Chlamydia trachomatis (xi) SEQUENCE DESCRIPTION: SEQ ID NO:25:

TTTTGGCCGC TAGAAAAGGC GATTTAAAAA CCAAGGTCGA TGTGATAGGG                  50

(2) INFORMATION FOR SEQ ID NO:26:

(i) SEQUENCE CHARACTERISTICS:
          (A) LENGTH: 50 base pairs
          (B) TYPE: nucleic acid
          (C) STRANDEDNESS: double
          (D) TOPOLOGY: linear (ii) MOLECULE TYPE: DNA (genomic)

(vi) ORIGINAL SOURCE:
          (A) ORGANISM: Chlamydia trachomatis (xi) SEQUENCE DESCRIPTION: SEQ ID NO:26:

CCCTATCACA TCGACCTTGG TTTTTAAATC GCCTTTTCTA GCGGCCAAAA                  50

(2) INFORMATION FOR SEQ ID NO:27:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:27:

CGCCTTTTCT AGCGGCCAAA A                                                21

(2) INFORMATION FOR SEQ ID NO:28:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:28:

TTTTGGCCGC TAGAAAAGGC GATT                                             24

(2) INFORMATION FOR SEQ ID NO:29:

(i) SEQUENCE CHARACTERISTICS:
          (A) LENGTH: 23 base pairs
          (B) TYPE: nucleic acid
          (C) STRANDEDNESS: single
          (D) TOPOLOGY: linear

```
    (ii) MOLECULE TYPE: DNA (genomic)

(xi) SEQUENCE DESCRIPTION: SEQ ID NO:29:

CCCTATCACA TCGACCTTGG TTT                                            23

(2) INFORMATION FOR SEQ ID NO:30:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

ACCAAGGTCG ATGTGATAGG G                                              21

(2) INFORMATION FOR SEQ ID NO:31:

(i) SEQUENCE CHARACTERISTICS:
        (A) LENGTH: 57 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Human papillomavirus (xi) SEQUENCE DESCRIPTION: SEQ ID NO:31:

CTGTTGTTGA TACTACACGC AGTACAAATA TGTCATTATG TGCTGCCATA TCTACTT       57

(2) INFORMATION FOR SEQ ID NO:32:

(i) SEQUENCE CHARACTERISTICS:
        (A) LENGTH: 57 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Human papillomavirus (xi) SEQUENCE DESCRIPTION: SEQ ID NO:32:

AAGTAGATAT GGCAGCACAT AATGACATAT TTGTACTGCG TGTAGTATCA ACAACAG       57

(2) INFORMATION FOR SEQ ID NO:33:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

AAGTAGATAT GGCAGCACAT AATGAC                                         26

(2) INFORMATION FOR SEQ ID NO:34:

(i) SEQUENCE CHARACTERISTICS:
        (A) LENGTH: 27 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO:34:

TTGTACTGCG TGTAGTATCA ACAACAG                                    27

(2) INFORMATION FOR SEQ ID NO:35:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

CTGTTGTTGA TACTACACGC AGTAC                                      25

(2) INFORMATION FOR SEQ ID NO:36:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

TGTCATTATG TGCTGCCATA TCTACTT                                    27

(2) INFORMATION FOR SEQ ID NO:37:

(i) SEQUENCE CHARACTERISTICS:
        (A) LENGTH: 58 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Hepatitis B virus (xi) SEQUENCE DESCRIPTION: SEQ ID NO:37:

CAGTTATATG GATGATGTGG TATTGGGGGC CAAGTCTGTA CAGCATCTTG AGTCCCTT   58

(2) INFORMATION FOR SEQ ID NO:38:

(i) SEQUENCE CHARACTERISTICS:
        (A) LENGTH: 58 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Hepatitis B virus (xi) SEQUENCE DESCRIPTION: SEQ ID NO:38:

AAGGGACTCA AGATGCTGTA CAGACTTGGC CCCCAATACC ACATCATCCA TATAACTG   58

(2) INFORMATION FOR SEQ ID NO:39:

(i) SEQUENCE CHARACTERISTICS:
        (A) LENGTH: 27 base pairs
        (B) TYPE: nucleic acid
        (C) STRANDEDNESS: single -continued (D) TOPOLOGY: linear (ii) MOLECULE TYPE: DNA (genomic)

(xi) SEQUENCE DESCRIPTION: SEQ ID NO:39:

AAGGGACTCA AGATGCTGTA CAGACTT                                            27

(2) INFORMATION FOR SEQ ID NO:40:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

CCAATACCAC ATCATCCATA TAACTG                                             26

(2) INFORMATION FOR SEQ ID NO:41:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:41:

CAGTTATATG GATGATGTGG TATT                                               24

(2) INFORMATION FOR SEQ ID NO:42:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

GAAGTCTGTA CAGCATCTTG AGTCCCTT                                           28

REPAIR-MEDIATED PROCESS FOR AMPLIFYING AND DETECTING NUCLEIC ACID SEQUENCES

This specification is a continuation of Ser. No. 07/841,649 filed Feb. 20, 1992, now abandoned, which is a continuation-in-part of Ser. No. 07/784,749 filed Oct. 28, 1991, now abandoned, which is a continuation of Ser. No. 07/221,750 filed Jul. 20, 1988, now abandoned, each of which is incorporated herein by reference.

FIELD OF THE INVENTION

The present invention is related to a process for amplifying and detecting existing nucleic acid sequences if they are present in a test sample. More specifically, it is related to a process for producing any particular nucleic acid sequence from a given sequence of DNA or RNA in amounts which are large, when compared to the amount initially present. The DNA or RNA may be single or double-stranded, and may be a relatively pure species or a component of a mixture of nucleic acids. The process of the invention utilizes a repetitive reaction to accomplish the amplification of the desired nucleic acid sequence.

BACKGROUND OF THE INVENTION

For diagnostic applications in particular, the target nucleic acid sequence may be only a minute portion of the total pool of DNA or RNA in a sample to be screened, so that it may be difficult to detect the presence of the target nucleic acid sequence using nonisotopically labeled or end-labeled oligonucleotide probes. Thus, diagnostic tests employing DNA probes to detect rare species of nucleic acids are often not sensitive enough to be practical for use outside of the research laboratory.

One attempt to overcome the sensitivity problem is the polymerase chain reaction (PCR) method, described in U.S. Pat. Nos. 4,683,195 and 4,683,202 ("the '195 and '202 patents"). This method proceeds basically, as follows:

a) treating a sample suspected of containing the target nucleic acid sequence of interest with one oligonucleotide primer for each strand of the target nucleic acid sequence, under hybridizing conditions and in the presence of a polymerase, e.g., the Klenow fragments of Escherichia coli DNA polymerase I, such that an extension product of each primer is synthesized if the target nucleic acid sequence is present;

b) placing the sample after step (a) under denaturing conditions to separate any primer extension products that are synthesized from the templates on which they are synthesized to produce single-stranded molecules;

c) treating the single-stranded molecules generated from step (b) with the primers of step (a) under the conditions of step (a), such that the new primer extension products are synthesized using both the original target sequences and the primer extension products produced in step (a) as templates, thus resulting in the amplification of the target nucleic acid sequence.

Steps (a)–(c) may be conducted sequentially or simultaneously. In addition, steps (b) and (c) may be repeated until the desired level of sequence amplification is obtained. As discussed in U.S. Pat. Nos. 4,683,195 and 4,683,202, the product of step (c) may be detected using probes.

The PCR method has a disadvantage in that it fails to completely overcome the sensitivity problem. The PCR method uses all four nucleotide bases to extend the primer fragments. Therefore, extension products may be created from other, non-target nucleic acid templates that may be present in the sample such as nicked, double-stranded DNA. The use of the PCR method results in considerable background of amplified DNA other than the target sequence(s).

As will be discussed in detail later, the present invention uses at least two oligonucleotides for each strand of target nucleic acid sequence and uses fewer than all four bases, thus reducing the problem of nonspecific, background amplification for a number of reasons. For example, when labeled nucleotides are used, the gap will be filled with labeled nucleotides if the nucleic acid target sequence exists in the sample and the irrelevant sequences will not be copied or labeled.

The polymerase chain reaction method also requires heat stable enzymes for the process to be automated, while the process of the present invention can be performed using heat-labile enzymes or without any enzymes, depending upon the particular embodiment. In addition, the detection of amplified nucleic acids produced in the PCR method often requires the use of gels or a capturing system, which are laborious detection methods. In contrast, the detection of the amplified sequences in the present invention is relatively simple. For example, a Sephadex column can be used to separate the joined, oligonucleotide products formed when the target sequence is present apart from the individual nucleotides.

Other methods, beside the PCR method, exist for producing nucleic acids in large amounts from initially small amounts. For example, there is the method of subcloning a nucleic acid in the appropriate host system, where the desired nucleic acid is inserted into an appropriate vector which is used to transform the host. When the host is cultured, the vector is replicated, and hence more copies of the desired nucleic acid are produced. For a brief description of subcloning nucleic acid fragments, see Maniatis, T., et al., Molecular Cloning; A Laboratory Manual, Cold Spring Harbor Laboratory, pp. 390–401 (1982). See also the techniques described in U.S. Pat. Nos. 4,416,988 and 4,403,036.

Other methods for synthesizing nucleic acids include the organic synthesis of a nucleic acid from nucleotide derivatives such as the methods described in U.S. Pat. No. 4,356,270. Another example of the method for synthesizing nucleic acid is provided in U.S. Pat. No. 4,293,652, which is a hybrid of organic synthesis and molecular cloning. The discussion of these and other methods in the '195 and '202 patents, as well as the patents listed above, are incorporated herein by reference.

SUMMARY OF THE INVENTION

The present invention relates to a process for amplifying one or more specific target nucleic acid sequences present in a sample.

In one embodiment of the present invention, the amplification is accomplished by using two or more oligonucleotide complement pairs wherein at least one strand of these oligonucleotide pairs has a nucleotide sequence complementary to at least a portion of the target sequence. The oligonucleotides are selected so there is a gap of at least one base when the complementary strands of the "oligonucleotide complement pairs" and the target nucleotide are hybridized to one another. The gap between the oligonucleotide complement sequences is filled by a mixture of polymerase and ligase producing an oligonucleotide repair product. The resulting mixture of hybridized molecules is then placed under denaturing conditions.

After the strands separate during denaturation, the ligated oligonucleotide product can hybridize to its complementary strands from other oligonucleotide complement pairs, and then the gap is filled again. The process is repeated as often as is necessary to produce the desired amount of oligonucleotide repair product. In one embodiment of the present invention, the enzymes are immobilized on a polymeric support.

The present method is especially useful for amplifying sequences indicative of a genetic disorder and rare species of nucleic acid present in a mixture of nucleic acids, and further permits the effective detection of such nucleic acid sequences. The present invention provides a process for amplifying at least one specific nucleic acid sequence in a sample of a nucleic acid or a mixture of nucleic acids. Each nucleic acid target could consist of one strand (RNA) or two separate complementary strands (DNA) of equal or unequal length.

The process is accomplished as follows:

a) Treating the sample with oligonucleotide complement pairs A,A' and B,B' under hybridizing and gap filling conditions. A is an oligonucleotide and A' is an oligonucleotide that is complementary to A. B is an oligonucleotide and B' is an oligonucleotide that is complementary to B. When the set of two pairs A,A' and B,B' are hybridized to nucleic acid target, A and B, which hybridize to one strand of the target forms a gap of one or more bases between them. Also, A' and B' form a gap of one or more bases between them. The gap is filled with labeled or unlabeled base(s) such that A and B become one strand with a continuous base sequence with one or more extra labeled or unlabeled bases, (A-Q-B), where Q is(are) the base(s) that fill the gap. Q could also be a base modified to be resistant to degradation caused by the 3'→5' exonuclease activity of polymerases used to fill the gap. Also, A' and B' are now one strand with a continuous base sequence with one or more extra labeled or unlabeled bases, (A'-Q'-B'), where Q' is(are) the base(s) that fill the gap. Similarly, Q' could also be one or more modified bases resistant to degradation caused by the 3', 5' exonuclease activity of polymerases. For any continuous base sequence A-Q-B or A'-Q'-B', Q or Q' can be composed of only one set of base pairs for any specific sequence, i.e., A-T, AU, G-C, or derivatives of these bases. A-Q-B and A'-Q'-B' are now joined, oligonucleotide products and can now serve as "target" sequences for other oligonucleotide complement pairs. When the joined, oligonucleotide product is formed by this gap-filling, ligated process it is termed an "oligonucleotide repair product."

b) Treating the sample under denaturing conditions to separate the oligonucleotide repair products from their targets, if the nucleic acid target sequence(s) is(are) present.

c) Treating the sample as in step (a) with oligonucleotide complement pairs A,A' and B,B' under hybridizing and gap-filling conditions such that an oligonucleotide repair product is obtained using each of the single strands produced in step (b), resulting in the amplification of the specific nucleic acid target sequence(s) if present.

The steps may be conducted sequentially or simultaneously. In addition, steps (b) and (c) may be repeated until the desired level of sequence amplification is obtained.

In another embodiment of the present invention, photosensitive molecules, x and y, are attached to each strand of the oligonucleotide complement pairs at the ends of the molecules which are to be joined together. X and y are compounds capable of forming carbon-carbon double bonds and undergoing [2+2] photocyclodimerization, thereby linking the oligonucleotide products when photoactivated and forming a joined, oligonucleotide product termed "an oligonucleotide photocylodimerizied product." In this embodiment, a gap between contiguous nucleotide strands is unnecessary. A gap of one or two bases is permissible.

This invention is also related to methods for the detection of the amplified specific nucleic acid sequence and diagnostic kits applicable thereto.

BRIEF DESCRIPTION OF THE DRAWINGS

FIG. 3 shows the titration of genomic cervical HPV16 DNA targets obtained from a biopsy. (Example 19).

FIG. 4 shows capture assay results of a titration of three samples containing DNA sequences 734–791 of the HBV genome (Example 20).

DETAILED DESCRIPTION OF THE PREFERRED EMBODIMENTS

Definitions

Figure 1:
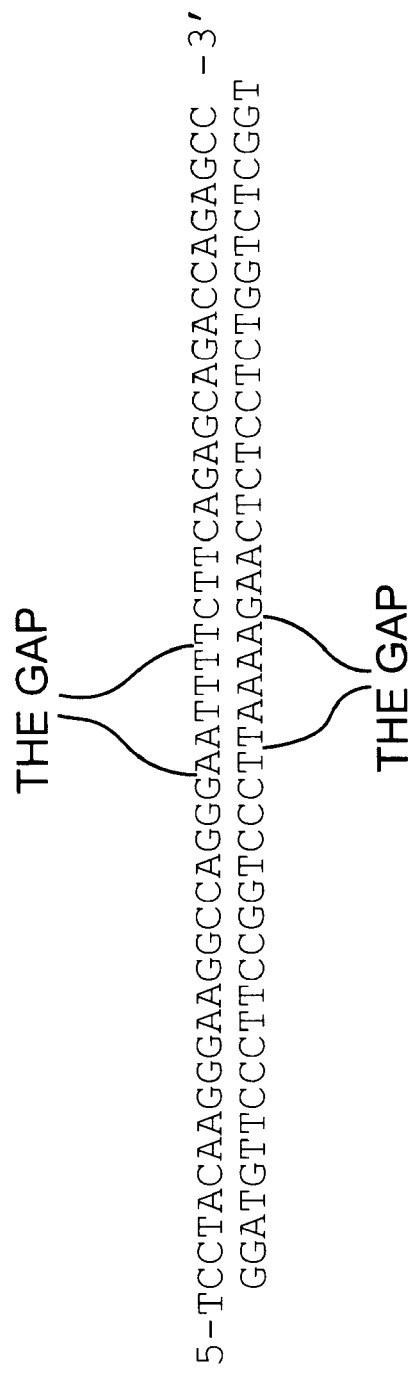
FIG. 1 illustrates a 48 base pair length sequence of HIV from GAG region desired to be amplified. The base pairs which fill the gap is depicted above and below the 48 base pair. (Example 1).

The term "oligonucleotide" as used herein, is defined as a molecule comprised of three or more deoxyribonucleotides or ribonucleotides, preferably more than five.

The term "blunt end" is defined as two oligonucleotides that have sequences complementary to each other and at least one end of equal length when hybridized together.

"Sticky end" as defined in this application refers to two oligonucleotides that have sequences complementary to each other and at least one end of unequal length when hybridized together. The categories of blunt end and sticky end are illustrated below.

The term "two oligonucleotide complement pairs" are at least four different oligonucleotides which are designated, for example, A,A' and B,B' wherein oligonucleotide A has a base sequence complementary to A', and oligonucleotide B has a base sequence complementary to B'. Each pair could be equal or unequal in length, which is illustrated as follows:

Category 1. Oligonucleotide Complement Pairs with Blunt Ends

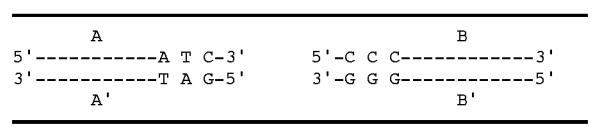

Category 2. Oligonucleotide Complement Pairs Each Having One Blunt and One Sticky End

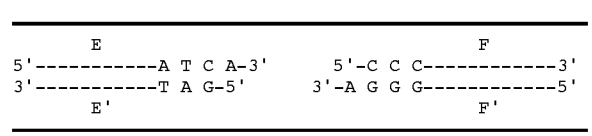

Two oligonucleotide complement pairs with a sticky end on one end of each pair are preferred as the bases for forming the collection of amplified oligonucleotides of the present invention. It would be understood that more than two oligonucleotide pairs could be used in the process of the present invention.

The term "gap" as used herein refers to the absence of one or more bases between A and B, E and F, or between A' and B', E' and F'. If more than two pairs are used then there may be more than one gap. The gap is created when the pairs are hybridized to the nucleic acid target, as for example:

```
Line 1: 5'-------------ATCATATCCC-------------3'
Line 2: 3'-------------TAG     GGG-------------5'
                          (the gap)
```

Line 1 is the sequence of the nucleic acid target, and line 2 represents oligonucleotide complements A' and B', as hybridized to the nucleic acid target sequence. If the target sequence is double-stranded, oligonucleotides A and B will form a hybrid with the sequence complementary to the target sequence shown above in line 1.

A. Gap-Filling, Ligation Amplification

In one embodiment of the process for amplifying nucleic acid sequences of the present invention, at least two oligonucleotide complement pairs are combined with the sample suspected or known to contain the target nucleic acid sequence of interest under hybridizing conditions. The oligonucleotide complement pairs are selected so that there is a gap in the nucleotide sequence of at least one base between the two complements when the two complements are hybridized with the nucleic acid target sequence. The gap is then filled and the two oligonucleotides are ligated together, producing an oligonucleotide repair product. The process of gap-filling plus ligation is analogous to the repair of mismatched bases, and other errors that occur during DNA replication, repair of UV damage, and other processes in vivo. The nucleic acid target sequence and the oligonucleotide repair product sequence may then be separated and the process repeated over and over again until the desired level of amplification has been achieved. To avoid a problem of background synthesis occurring during the gap filling step, the two or more oligonucleotide complement pairs are selected so that the gaps between them will require less than all four bases to fill in the gap, preferably one set of complementary bases, namely AT, AU, or GC. Without all four bases, random synthesis would not be initiated by nucleic acid sequences that may have nicks or are in the process of replication or transcription.

1. Nucleic Acid Target Sequences

The process of the present invention can produce exponential quantities of at least one specific nucleic acid sequence relative to the number of reaction steps involved, provided that (a) at least part of the nucleic acid target sequence is known in sufficient detail that oligonucleotide pairs can be synthesized which can hybridize to it, or (b) the target sequence can be isolated in large enough quantities to produce enough oligonucleotide complement pairs for use in the process. Any source of nucleic acid can be utilized as the source of the target nucleic acid sequence, in purified or nonpurified form. For example, the process may employ either single-stranded or double-stranded DNA or RNA. In addition, a DNA-RNA hybrid which contains one strand of each may be utilized. A mixture of any these nucleic acids may be employed. The specific nucleic acid sequence to be amplified may be only a fraction of a larger molecule. It may be a minor fraction of a complex mixture, such as a portion of the HIV (human immunodeficiency virus) gene integrated in the genomic DNA of an infected person, or bacterial nucleic acid present in very low quantities in a particular biological sample.

To determine the sequence of the target sequence(s), or as a sample to be tested, the nucleic acid or acids of interest may be obtained from any source, for example, DNA or RNA, isolated from bacteria, viruses, yeast and higher organisms such as plants or animals, from plasmids such as PBR 322 and M13, from cloned DNA or RNA by a variety of techniques known to those skilled in the art. DNA may also be extracted from cells grown in tissue culture by techniques such as those described by Maniatis et al., Molecular Cloning, a Laboratory Manual (New York: Cold Spring Harbor Laboratory, 1982), pp.280–281.

2. oligonucleotide Complement Pairs

The oligonucleotide complement pairs are preferably oligodeoxyribonucleotides. In addition, the pairs must be long enough to hybridize to the nucleic acid target sequence(s). The length of the complement pairs can vary from four bases to hundreds of bases. A short oligonucleotide generally requires cooler temperatures to form stable, hybrid complexes. The oligonucleotide sequences synthesized are selected so that two oligonucleotide complement pairs would both hybridize to the target sequence and yet leave a gap of one or more bases. If the target sequence is single-stranded, only one half of each oligonucleotide pair would hybridize to the target. More than two pairs of oligonucleotide complements can be employed in the process of the invention as long as the amplification will remain specific for the nucleic acid target sequence(s).

The oligonucleotide complement pairs may be prepared using any suitable method, e.g., phosphoramidites (Applied Biosystems Inc.) may be used as starting materials and may be synthesized as described by Beaucage, et al., Tetrahedron Letters, 22, 1859–62 (1981) and phosphorylated at 5'-end by methods well-known in the art.

3. Denaturation

The strand separation can be accomplished by any suitable denaturing method including physical, chemical or enzymatic means. One physical method of separating the strands of the nucleic acid involves heating the nucleic acid until it is completely (more than 99%) denatured. Typical heat denaturation may involve temperatures ranging from about 80° C. to 105° C., for times ranging from about 1 to 10 minutes. Strand separation may also be induced by an enzyme from the class of enzymes known as helicases or the enzyme RecA, which has helicase activity and in the presence of riboATP is known to denature DNA. The reaction conditions suitable for separating the strands of nucleic acids with helicases are described by Cold Spring Harbor Symposia on Quantitative Biology, Vol. XLIII "DNA Replication and Recombination" (New York: Cold Spring Harbor Laboratory, 1978), B. Kuhn et al., "DNA Helicases", pp. 63–67, and techniques for using RecA are reviewed in C. Radding, Ann. Rev. Genetics, 16:405–37 (1982).

4. Gap-Filling/Ligation steps

Generally, the gap-filling and ligation steps occur in a buffered aqueous solution, preferably at a pH of 7–9, most preferably at a pH 7.5. The oligonucleotide complement pairs will be present in molar excess of about $10^5$–$10^{15}$, preferably $10^9$–$10^{15}$, pairs per nucleic acid target sequence. The exact amount of the pairs to be used in diagnostic purposes may not be known due to uncertainty as to the amount of the nucleic acid target in a sample. However, using an average amount of $10^{15}$ oligonucleotide complement pairs is applicable in a typical diagnosis assay format. A large molar excess is preferred in any case to improve the efficiency of the process of the invention.

In the process of the invention, typically only two complementary deoxyribonucleoside triphosphates would be used in the gap-filling step, dATP and TTP, or alternatively, dCTP and dGTP. Sticky-ended oligonucleotide complement pairs can be selected, so that only one type of deoxyribonucleoside triphosphate is required to fill in any gaps. Sticky-ended complement pairs can also be selected so that two complementary nucleotides and one other nucleotide are used to fill the gap.

It is preferred to utilize modified nucleoside triphosphates known in the art to be resistant to the exonuclease activity of polymerases, as described by D. Shortle et al., Proc. Natl. Acad. Sci. USA, 79: 1588–92 (1982); T. A. Kunkel, ibid., 78: 6734–38, (1981); F. R. Bryant et al., Biochemistry 18: 2825–28 (1979). Such molecules could be thymidine 5'-O-(1-thiotriphosphate) (TTP [alpha-S]), 2'-deoxyadenosine 5'-O-(1-thiotriphosphate) (dATP [alpha-S]) and the thio-derivatives of deoxycytidine, deoxyguanidine, deoxyuridine and of cytidine, guanidine, adenosine, thymidine, and uracil. Other derivatives of these bases that are resistant to nuclease activity are suitable, such as alpha-imido derivative of triphosphate bases.

Sufficient deoxyribonucleotide triphosphates are added to the gap-filling/ligating mixture in adequate amounts and the resulting solution is heated to about 90° C. to 100° C. for approximately one to five minutes, preferably from one to three minutes. The solution is then allowed to cool to room temperature to allow hybridization to occur. To the cooled solution, appropriate catalysts are added to induce the filling and sealing of the gap under conditions known in the art. For example, known DNA polymerases can be used for the gap-filling and known DNA ligases can join the resulting product after the polymerase has filled the gap. The gap-filling ligation process may occur at from 4° C. up to a temperature at which the catalytic agents no longer function efficiently; the temperature is generally no greater than about 40° C. Thus, for example, if T4-DNA polymerase and T4-DNA ligase are used, the temperature is generally no greater than about 40° C. (most conveniently, the reaction occurs at room temperature or even at 4° C.). If heat insensitive enzymes are used, then the process could occur at the melting temperature of the hybrids templates.

The catalytic agent may be any compound or system which will function to fill the gap between the two or more oligonucleotides hybridized to the nucleic acid target. Enzymes suitable for this purpose include *E. coli* DNA polymerase-I, Klenow fragment of *E. coli* DNA polymerase-I, T4-DNA polymerase, reverse transcriptase for adding bases to fill in the gap, T4-DNA ligase to join the oligonucleotide(s), plus nucleotides added by the polymerase, to the other oligonucleotide complements, forming a joined oligonucleotide product, which in this embodiment is termed the oligonucleotide repair product.

The oligonucleotide repair products hybridized to the nucleic acid targets are in a double-stranded form. In the next step, the strands of the double-stranded molecule are again separated as described above to provide single-stranded molecules.

In order to generate a mode of amplification, the joined oligonucleotide molecules can hybridize to two more oligonucleotide complement pairs. If necessary, additional enzymes, appropriate deoxyribonucleotide triphosphates, and oligonucleotides may be added for the reaction to proceed.

The steps of strand separation, gap-filling and ligation can be repeated as often as needed to produce the desired amount of the specific joined, oligonucleotide product assuming that one copy of single-stranded nucleic acid target sequence is present in the mixture at the beginning. As long as these steps will be repeated, the amplification of the specific nucleic acid target sequence will take place in an exponential way. This process could be used to amplify other nucleic acid target sequences, by adding different oligonucleotide complement pairs (or triplets, etc.) that hybridize to different specific nucleic acid target sequences without changing other conditions involved.

This particular embodiment of the invention could be performed in a stepwise fashion, in which new reagents are added after each step, or simultaneously, in which all reagents are added at once. The reagents can also be added after a given stage. Each step of the embodiment using heat-stable enzymes will occur sequentially regardless of the initial concentration of all the reagents. When heat-sensitive enzymes are used, it is necessary to add the gap-filling and sealing agents after every strand separation (denaturation) step.

In one embodiment of the present invention, the catalytic agents are immobilized on polymeric supports. After the gap-filling and ligation step, the products can be eluted from the immobilized enzymes and denatured to single strands. At this point, the nucleic acid target sequence(s) and joined, oligonucleotide product(s) are available to form hybrids with additional, oligonucleotide complement pairs. These new hybrids are then transferred back to the immobilized enzymes to form joined products. The steps of the reaction may be carried out stepwise or simultaneously and may be repeated as often as desired.

For smaller oligonucleotide complements, for example, 6–10 bases, heat-sensitive enzymes could be employed in a simultaneous procedure, since the melting temperature of double-stranded oligonucleotides of this range is around 40° C., and heat-sensitive enzymes are active at this temperature.

If heat-stable gap-filling and sealing agents are used, such as thermostable polymerase and ligase, then the process could be employed at an elevated temperature, preferably 60–90° C. depending on the heat-stable enzymes. The temperature would also be determined by the temperature at which there will be an equilibrium between single and double-stranded nucleic acids. A heat-stable polymerase and ligase could be extracted from *Thermus thermophilus*. Such a heat-stable polymerase is described by A. D. Kaledin, et al., Biokhimiya, 45, 644–51 (1980). A heat-stable ligase is described by M. Takahashi et al., J. Biol. Chem., 259 (16), 10041–10047 (1984).

After the appropriate period of performing the process has passed, and the desired amount of the oligonucleotide repair product has accumulated, the reaction may be stopped by inactivating the enzymes in any known manner or separating the components of the reaction on spun or Sephadex columns, by filtration, or by gel electrophoresis as known in the art.

The process of this invention may be employed as an automated process. To do this, the reaction is cycled through a denaturing step, a reagent addition step, and a reaction step. Also the process may be conducted continuously by adding the reagents automatically by a pump after the denaturing step, while the heating-cooling step could be performed by a specially designed, controlled heater block.

The present invention is demonstrated diagrammatically below. Using two oligonucleotide complement pairs that have one sticky end each (Category 2.)

Two Sticky-Ended Pairs

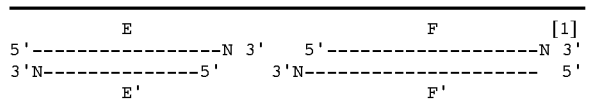

N is a nucleotide modified to protect the strands from degradation by 3' exonucleases, such as that found as part of T4-DNA polymerase. oligonucleotide complement pairs E, E' and F, F' are selected or synthesized to correspond to sections of the complete nucleic acid target sequence R. R is a double-stranded DNA comprising complementary strand R+ and R− represented as:

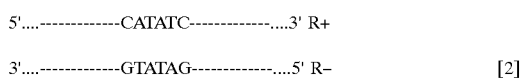

When [R] is mixed with a molar excess oligonucleotides of complement pairs E, E' and F, F' under conditions where the double-stranded molecules are denatured and then are permitted to rehybridize, R+ forms stable, double-stranded hybrids with E' and F', while R− forms hybrids with E and F as illustrated by:

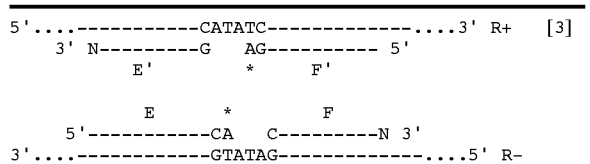

A * represents the modified nucleotide N of diagram [1] such as [NTP's alpha-S].

Next, TTP, dATP, E. coli. Klenow fragment and T4-DNA ligase are added to mixture, permitting the gap in the double strands to be filled and sealed, producing:

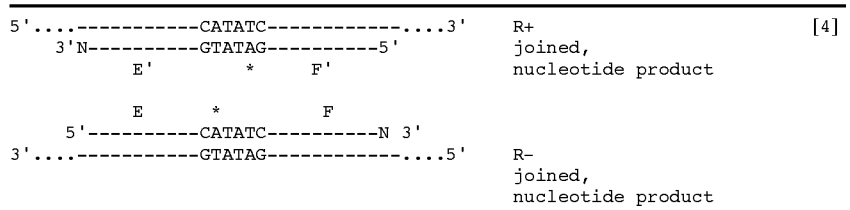

In this particular example, the Klenow fragment adds the nucleotides to the 3' of F' and the ligase joins the added nucleotides to the 5' end of E', E and F are joined in the same fashion.

In the first cycle, two new single-stranded DNA have been produced. After the next denaturing step, the molar excess of the two oligonucleotide complement pairs can hybridize to the original nucleic acid targets as well as to the oligonucleotide repair product formed in the first cycle, thus four more oligonucleotide repair products are formed in the second cycle. The formation of the new joined oligonucleotides product will proceed exponentially.

In this process, dATP and TTP could be labeled with radioactive labels, such as $^{32}P$, $^{35}S$, or $^{125}I$. Non-radioactive labels can also be used. For example, TTP could be replaced by Biotin-dUTP (Enzo Biochem), and dATP could be replaced by Biotin-dATP as described by G. Gebeyehu et al., Nucleic Acid Res. 15, 4513–34 (1987).

In the case when blunt-ended oligonucleotide pairs in solution are used (category 1), blunt-end ligation could occur between the set of two pairs in solution. However, since only the bases which filled the gap are labeled, the blunt end ligation products will not be counted in the detection step.

B. Photochemical Ligation

In another embodiment of the present invention, photosensitive molecules, x and y, that can form carbon—carbon double bonds and undergo [2+2] photocyclodimerization are employed to link the oligonucleotide complements together. The photosensitive molecules x and y are attached to each strand of the oligonucleotide complement pairs at the ends of the molecules which are to be joined together. X (or X') and y (or y') can be the same molecules or different ones, as long as the photocyclodimerization reaction can occur. This embodiment of the invention can be illustrated as:

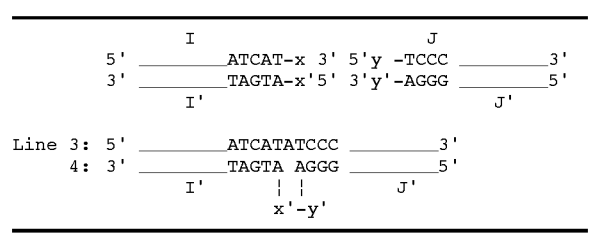

Line 3 represent the sequence of the nucleic acid target, and line 4 represent oligonucleotides I' and J' hybridized to the nucleic acid target sequence. If the target sequence is double-stranded, oligonucleotides I and J will form a hybrid with the sequence complementary to the target sequence shown in line 3. After the hybrids with the target sequence is formed, x' and y' are photoactivated, as will be described in detail later, producing a photodimer, thereby joining oligonucleotides I' and J' together.

In order to create such bonds, these photoactivatable groups should be in close proximity to each other (4° A separation) and nearly parallel, thus permitting excellent pi-electron overlap. This proximity provides strong attractive interaction when one of the molecules is excited, Schmidt et al., Pure Appl. Chem., 27: 647–78 (1971). Without the close proximity, the photoactivable molecules are too far apart and/or unsuitably oriented to form the double bonds necessary to create stereoisomeric photodimers. Consequently, no photochemical ligation between oligonucleotide complements pairs in solution are likely to occur. Rather, the photoactivatable groups, x and y, will only be close enough to each other to bond together when the complements are hybridized to the nucleic acid target sequence or to a joined, oligonucleotide target created in a previous cycle.

Photosensitive molecules, x and y, that can form carbon-carbon double bonds and undergo [2+2] photocyclodimerization are useful in this embodiment of the present invention. These photosensitive molecules can include: cinnamic acids, M. D. Cohen et al., J. Chem. Soc., 2000–13 (1964); T. Ishigami, et al., Bull. Chem. Soc. Japan, 49: 3578–83 (1976); styrene derivatives, A. L. Elgavi, et al., Thesis, Weizmann Institute of Science, Rehovot, Israel (1974); stilbenes, M. D. Cohen, et al., J. Chem. Phys. Lett. 7: 486–90 (1970); aliphatic mono-, di- and triene dicarboxylic acid derivatives, T. J. Sadeh, Am. Chem. Soc. 84: 3970 (1962); M. J. Lahav, Chem. Soc. B., 312–17 (1967); M. Lahav, Tetrahedron Lett. 2957–62 (1966), cross-conjugated aromatics, B. S. Green, Tetrahedron Lett., 4249–52 (1970); benzoquinones, D. Rabinovich, et al., J. Chem Soc. B., 144–49 (1967); allenes, Z. Berkovitch-Yellin, et al., J. Chem. Soc. Chem. Comm., 178–79 (1982); and psoralenes. In other words, x and y are any molecules that are capable of absorbing light and thereby creating cyclobutane derivatives.

The x and y moieties are preferably aminopsoralenes or coumarines that have a tendency to form a complex that overlaps and therefore facilitates the [2+2] photocylodimerization. Moreover, psoralenes are photoactivated at 320–460 nm wavelength, which is a wavelength that does not damage the nucleic acids in the sample. The oligonucleotide complements must be sufficiently long enough to form a stable hybrid with the target in order to reach the proper proximity and the maximum pi-electron overlap between x and y. As used herein, the term "light source" refers to an irradiation source that could excite pi→pi *, n→pi * in the range of 200 nm–500 nm, preferably in the range of 300 nm–400 nm, where the source is near U.V. light or ultraviolet laser pulses. The creation of the new bond, by using a light source, takes place in a buffered aqueous solution, at a pH of 7–9, preferably at pH 8.

Particularly, preferred photoactivatable molecules, x and y, for use in the process of the present invention are the following:

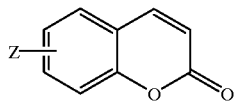

Coumarin derivatives where Z is H, methoxy, acetoxy, C1–C5 alkyl, halogen and di or tri derivatives of these groups;

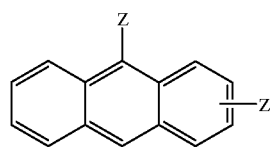

Anthracene derivatives where Z is H, CN, alkyl or halogen;

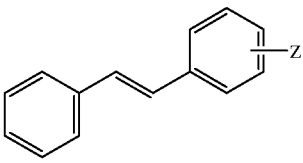

Stilbene derivatives where Z is H, CN, alkyl, halogen, $CO_2H$, or alkyl ester;

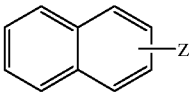

Naphthalene derivatives where Z is H, CN, —O—Alkyl, halogen or carboxy;

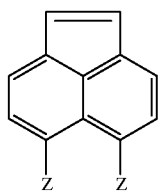

Acenaphthylene derivatives where Z is H, CN, alkyl, halogen, or carboxy.

The photoreactive molecules may be attached to the oligonucleotides at the 5' and 3' ends using any of the following methods:

a) Modification of 5'-hydroxyl group by amines as described by L. M. Smith et al., Nucleic Acid Res. 13: 2399 (1985), by 5'-thiols as described by B. S. Sproat et al., Nucleic Acid Res., 15: 4837 (1987), by phosphate group using T4-DNA ligase, by chemical phosphorylation as described by T. Horn et al., Tetrahedron Lett. 27: 4705 (1986), or by other methods of modifications.

b) Modification of 3'-hydroxyl group by amino group is described by U.S. Pat. No. 4,128,639. A 3'-phosphate group could be attached to the oligonucleotide using the same chemical phosphorylating agent, as described above by T. Horn et al.

The preferred method of attaching the photoreactive molecule to the 3' and 5' ends of the oligonucleotides is by attaching phosphate groups to the desired 3' and 5'-hydroxyl groups, e.g., the 3'-phosphate group is synthesized as follows: controlled pore glass (CPG) (500 Angstrom pore diameter) (PIERCE) that is modified with long chain alkyl amine is allowed to condense with a phosphorylating agent,

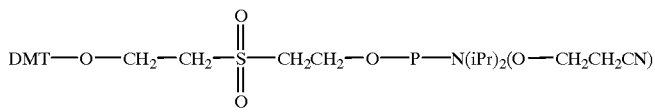

(Glen Corp.) (DMT is dimethoxytrityl; iPr is isopropyl), in the presence of tetrazol at ambient temperature. The phosphate group is then oxidized using an oxidizing agent, preferably iodine solution, at room temperature. After detritylation, using a mild acid, preferably dichloroacetic acid in dichloromethane, a hydroxyl group is exposed and the desired oligonucleotides could be synthesized on this hydroxyl group, as known in the art.

The 5'-phosphate group, attached to the desired oligonucleotides, could be prepared by ligation procedures under conditions known in the art. The 3' or 5'-end phosphate groups could be activated with activating agents, preferably imidazole, using a condensing agent, preferably water-soluble carbodiimide, at ambient pH, preferably pH 6.0, at room temperature.

The aminophotoreactive group is reacted with activated phosphate group at pH 7.8 as described by B. C. F. Chu et al. in Nucleic Acid Res., 11: 6513–29 (1983).

C. Detection of the Joined, Oligonucleotide Product

The joined, oligonucleotide product can be detected by any number of methods for detecting labeled molecules and/or molecules having a particular length or sequence. For instance, the reaction mix may be passed through a Sephadex column to separate the labeled NTPs and the joined oligonucleotide products. Since individual nucleotides are much smaller than the length of the two or more oligonucleotide complement pairs, the detection of amplified material should be fairly simple based on size alone.

Another technique to detect amplified sequence would require the construction or isolation of probes that share complementary sequences with enough of each and every oligonucleotide complement pair to bind and hold the joined product preferentially. Such probes can be immobilized on any suitable substrate. They may also be labeled differentially if desired.

The present invention may be used for in vitro diagnostics. The process of amplifying nucleic acid sequences enables the detection of specific nucleic acid sequences associated with infectious disease, genetic disorders or cellular disorders such as cancer. Amplification is particularly useful when the amount of nucleic acid target available for diagnosis is in minute quantities, as, for example, in the prenatal diagnosis of sickle cell anemia, which requires obtaining DNA from fetal cells. Furthermore, it is within the ability of those skilled in the art, that the length and sequences of the oligonucleotide complements can be varied to detect deletions and/or mutations in genomic DNA from any organisms. These small changes are important in the diagnosis of such conditions as cystic fibrosis, alpha-thalassemia, bata-thalassemia and the like.

The process of the invention may also indicate the presence of various agent like pathogenic viruses including human immunodeficiency virus (HIV), herpes, hepatitis B and bacteria including Salmonella and Chlamydia.

U.S. Pat. No. 4,358,535, issued to Falkow, describes the use of specific DNA hybridization probes for the diagnosis of infectious diseases. A problem inherent in the Falkow procedure is that a relatively small number of pathogenic organisms may be present in a clinical sample from an infected patient and the DNA extracted from the pathogens may constitute only a very small fraction of the total DNA in the sample. Specific amplification of suspected sequences in a sample prior to the hybridization to the probes and the immobilization on filters samples could greatly improve the sensitivity and specificity of these procedures.

In a further embodiment, the amplified species could be detected by a simple method as follows: A capture oligonucleotide probe that has a nucleic acid sequence which is complementary to both E and F or E' and F' or to each one of them separately could be used to capture the amplified labeled products.

In another embodiment, the deoxyribonucleotide triphosphates involved in the process could be radioactively labeled such as with $^{32}P$, $^{35}S$, $^{125}I$ and others with non-radioactive labeling.

Another means to facilitate the clinical use of DNA probes for the diagnosis of infectious diseases is the substitution of non-radioactive labels for radioactive ones. As described in EP 63,879 to Ward, biotin-containing DNA probes are detected by chromogenic enzymes linked to avidin or biotin-specific antibodies. This type of detection is convenient, but relatively insensitive. The combination of DNA amplification by the present method and the use of Bio-dUTP to label the bases that filled the gap could provide the convenience and sensitivity required to prepare useful diagnostic kits and to overcome the difficulties associated with both Falkow and Ward procedures when these techniques are applied in a routine clinical setting.

The use of the Falkow and Ward methods, the synthesis of oligonucleotides, the calculation of the number of sequences amplified per cycle, and other matters that pertain generally to amplification of nucleic acid sequences are described in the '195 and '202 applications and these applications are incorporated herein by reference.

The invention will now be illustrated by examples. The examples are not intended to limit the scope of the present invention. In conjunction with the general and detailed description above, the examples provide further understanding of the present invention and outlines some aspects of the preferred embodiments of the invention.

EXAMPLE 1

The desired sequence to be amplified using the gap-filling/ligating embodiment of joining the oligonucleotides is a 48 base pair sequence that coded for HIV at GAG region 2106–2153. This sequence is chosen for its G-C content which is about 52% and has the following sequence:

5'-TCCTACAAGGGAAGGCCAGGGAATTTTCTTCA-GAGCAGACCAGAGCC-3'
3'-GGATGTTCCCTTCCGGTCCCTTAAAAGAAGTCT-CGTCTGGTCTCGGT-5'
See SEQ ID NO's. 1–2.

The following four oligodeoxyribonucleotides are examples of the many blunted-ended sequences that can be used for amplification according to the method of the invention.
A—5'-TCCTACAAGGGAAGGCCAGGG-3'
A'—3'-GGATGTTCCCTTCCGGTCCCT-5'
B—5'-TCTTCAGAGCAGACCAGAGCC-3'
B'—3'-GAAGTCTCGTCTGGTCTCGGT-5'
See SEQ ID NO's. 3–6.

The blunt ends are created after incorporation of 2'-deoxyadenosine 5'-0-(1-thiotriphosphate) (dATP[alpha-S]) at the 3' end of each sequence. A gap of 5 base pair exists between the oligonucleotides A and B or A' and B' when these strands are hybridized to their complementary strand of the target sequence shown above.

Similarly, the following four oligodeoxyribonucleotides are suitable sticky-ended sequences that may be utilized in the process of the invention.
E—5'-TCCTACAAGGGAAGGCCAGGGA-3' 22 bases
E'—3'-GGATGTTCCCTTCCGGTCCCTTA-5' 22 bases
F—5'-TCTTCAGAGCAGACCAGAGCC-3' 21 bases
F'—3'-GAAGTCTCGTCTGGTCTCGGT-5' 21 bases
See SEQ ID NO's. 7–10.

All of oligodeoxribonucleotides described above are synthesized and purified by the following procedure.

I. Automated Synthesis Procedures.

The 2-cyanoethyl phosphoramidites are purchased from Applied Biosystems Inc. The procedure includes condensation of nucleside phosphoramidites to 30 mg of a nucleoside-derivatized controlled pore glass (CPG) bead support (500 Angstrom pore diameter), using DNA synthesizer from Applied Biosystems Inc., Type 380B-02. The cycles includes detritylation with 2% trichloroacetic acid in dichloromethane; condensation using tetrazol as an activating proton donor; capping with acetic anhydride and dimethylaminopyridine; detritylation using 2% trichloroacetic acid in dichloromethane; and oxidation of the phosphite to the phosphate with 0.1 M $I_2/H_2O$/lutidine/tetrahydrofuran. Cycle time is approximately 30 minutes. Yields at each step are essentially quantitative and are determined by collection and spectroscopic examination of the dimethoxytrityl alcohol released during detritylation.

II. Oligodeoxyribonucleotide Deprotection and Purification Procedures

The solid support is removed from the column and exposed to 1 ml concentrated ammonium hydroxide at 60° C. for 16 hours in a closed tube. Ammonia is removed and the residue is applied to a preparative 12% polyacrylamide gel using a Tris-borate buffer (pH 8) containing 7M urea. Electrophoresis is carried out at 20 volts/cm for 5 hours after which the band containing the product is identified by UV shadowing of a fluorescent plate. The band is excised and eluted with 1 ml double distilled water overnight at room temperature. This solution is filtered and the supernatant is extracted (3×300 microliter) with n-butanol. The water phase is placed on a Sephadex G50 column (Pharmacia) (1×10 cm). The elution is monitored by UV absorbance at 260 nm and the appropriate fraction collected, quantitated by UV absorbance in a fixed volume and evaporated to dryness at room temperature in a vacuum centrifuge.

III. 5'-Phosphorylation of A',B, E'and F sequences

In order to phosphorylate 5'-ends of A',B, E' and F, a new-phosphorylating reagent as described by T. Horn et al., Tetrahedron Letters 27: 4705–08 (1986) is used. Only the ends of the nucleotides that are to be joined together will be phosphorylated.

The synthesis of A',B, E' and F is described as in I. Automated Synthesis Procedure, but after the last cycle, the phosphorylating reagent

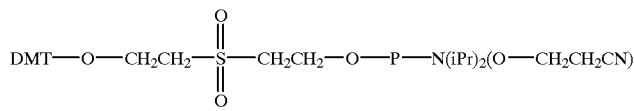

(Glen Corp. Inc.) (DMT is dimethoxytrityl group; iPr is isopropyl) is condensed to each of the sequences A',B, E' and F using tetrazol as an activating proton donor, followed by capping with acetic anhydride and dimethylaminopyridine; detritylation using 2% trichloroacetic acid in dichloromethane; and oxidation of the phosphite to the phosphate with 0.1M $I_2/H_2O$/lutidine/tetrahydrofuran. Cycle time is approximately 30 minutes.

The 5'-phosphorylated A', B, E' and F are purified and quantitated by the procedure described in II above.

EXAMPLE 2

This experiment illustrates the amplification of the 48 base pair sequence of Example 1 by using a set of two blunt-ended oligonucleotide complement pairs, where a gap of 5 bases (A,T) exists between the pairs. In the first step the polymerase will incorporate dATP[alpha-S] in order to protect the complement pairs from the 3' exonuclease activity of DNA polymerase I and to form blunt-ends.

Amplification of the 48 base pairs starts from step 2.

Step 1:

50 microliters containing 1 mM $MgCl_2$, 20 mM 2-mercaptoethanol, 100 mg of bovine serum albumin per ml, 0.1 mM ATP, and 0.1 mM of dATP[alpha-S]) (Sigma) are added to a 60 microliter buffer solution containing 50 mM Tris-HCl, pH 7.5.

To this solution are added 5 microliters of solution containing 100 picomoles each of A and B' and phosphorylated A' and B and 0.1 picomole of the 48 base pairs to be amplified. The resulting solution is heated to 100° C. for 2 minutes, which allows separation of the strands and hybridization of the A, A', B, and B' to the target. Then, 4 units of Klenow fragment of E. coli DNA polymerase-I are added and the reaction is incubated for 10 minutes at room temperature.

The two pairs are now blunt-ended and protected against exonuclease activity of polymerase.

Step 2:

In order to produce and amplify the joined, oligonucleotide products, the following sub-steps are employed.

a. Add 1 nanomole each of dATP and TTP and 100 picomoles of each of alpha-$^{32}$P-dATP and alpha-$^{32}$P-TTP (Specific activity 1000 cpm/picomole).

b. Heat for 2 minutes to 100° C.

c. Cool to room temperature for 2 minutes.

d. Add a mixture of 4 units of Klenow fragment of E. coli DNA polymerase-I and 2 units of T4-DNA ligase.

e. Incubate for 10 minutes at room temperature.

Sub-step (a) in the cycle can be omitted if a sufficient amount of nucleotide triphosphates are present initially. The cycle is repeated 22 times. 2 microliter aliquots from cycles 2, 4, 7, 10, 13, 16, 19, and 22 are applied to a 12% Polyacrylamide gel, 7M urea using 0.089 M Tris-borate buffer, pH 8.3. Electrophoresis is carried out at 20 volts/cm for 5 hours. The gel is exposed to sensitive film (Kodak) for 5 hours.

The resulting reaction mixture is loaded on a Sephadex G40/50 column (1×10 cm) (Pharmacia) and eluted with double distilled water. Two distinct peaks are separated and monitored by a Geiger counter. The first peak, appearing after elution of 5–7 ml of water, consists of the amplified 48 base pairs, and the second peak, appearing after elution of 14–18 ml of water, consists of alpha-$^{32}$P-dATP and alpha-$^{32}$P-TTP.

In this example, steps 1 and 2 are employed separately. However, the two steps can be combined into one step, so that the cycling could start immediately by using a mixture of dATP[alpha-S] that could be added in Step 2, sub-step (a) of the cycle, or, alternatively, the protected blunt-ended pairs could be prepared separately, purified, quantitated, and used as desired.

EXAMPLE 3

This example illustrates a non-radioactive labeling during the amplification protocol of this invention. 100 microliters solution containing 1 mM $MgCl_2$, 20 mM 2-mercaptoethanol, 100 mg of bovine serum albumin per ml and 50 mM Tris-HCl (pH 7.5). 5 microliters of a solution containing one nanomole of each of A, A', B, and B' where B and A' are phosphorylated at their 5'-ends, and 10 picomole of 48 base pair as prepared in Example 1 are added. 1 nanomole of each of dATP and Bio-11-dUTP (Enzo Biochem) and 100 picomoles of dATP [alpha-S] are also added. The number 11 designated a linker arm of 11 atoms.

The resulting solution is subjected to cycles as described above e.g., the mixture is heated to 100° C. for 3 minutes and allowed to cool to room temperature for 2 minutes, whereupon 4 units of Klenow-fragment of E. coli DNA polymerase-I and 2 units of T4-DNA ligase are added. The reaction mixture is incubated for 5 minutes at room temperature. The cycle is repeated 20 times as described in the previous experiment.

The reaction mixture is then diluted with 100 microliters of 2M ammonium acetate buffer, pH 7.5. The mixture is serially diluted 4-fold using 1M ammonium acetate as a diluent. Aliquots (50 microliters) of the amplified DNA solution is added to the wells of 96-well Dynatech Immulon II microtiter plates (Dynatech). The plates are sealed and incubated for 90 minutes at 37° C. to bind the amplified DNA to the plates. After the incubation, the wells are washed at room temperature twice with 200 microliters aliquots of 0.3M NaCl and 0.03M sodium citrate, pH 7.0, and once with 200 microliters of the same buffer containing 0.1% Triton X100. The wells are treated for 30 minutes at room temperature with aliquots (200 microliters) of a solution containing 10 mM sodium phosphate (pH 7.4), 0.5M NaCl, 2% BSA, 0.1% Triton X100 and 5 mM EDTA (blocking solution).

After removing of the blocking solution from the wells, aliquots (50 microliters) of a solution containing horseradish peroxidase-labelled avidin (Vector Labs) is added to each well. The peroxidase-labelled avidin is diluted in PBS, 0.1% Triton X-100 according to the manufacturer's instructions.

The plates are incubated for 30 minutes at room temperature, then washed (4×200 microliter) with a solution of 10 mM sodium phosphate (pH 7.4), 0.5 M sodium chloride 0.1% Triton X-100 and 5 mM EDTA and then (1×200 microliters) with PBS containing 1 mM EDTA.

The DNA-biotinylated probe-labelled avidin complexes are detected by adding to each well 150 microliters of a substrate reaction mixture containing 1.6 mg/ml o-phenylenediamine (Sigma) and 0.0125% hydrogen peroxide in 0.1 M sodium phosphate buffer adjusted to pH 6.0 by 0.05 M citric acid solution. The plates are incubated for 30 minutes at room temperature in the dark and then the reaction is stopped by the addition of 4 N sulfuric acid (50 microliters), The contents of the plates are read in an Intermed Immuno Reader NJ-2000 spectrophotometric plate reader at wavelength 490 nm.

The results are shown in Table 1:

TABLE 1

| Absorbance (O.D. 490) [Amplified DNA] | Control (a) |
|---|---|
| 1 nmole | over 0.019 |
| 0.5 nmole | over 0.025 |

TABLE 1-continued

| Absorbance (O.D. 490) [Amplified DNA] | Control (a) |
|---|---|
| 0.250 nmole | over 0.016 |
| 0.125 nmole | over 0.012 |

(a) Control means 100 picomoles of Bio-dUTP are fixed on the wells using ammonium acetate.

EXAMPLE 4

This example illustrates amplification using sticky-ended oligonucleotide complement pairs (E, E', F and F' as described). The desired sequence to be amplified is the same 48 base pair sequence as prepared in Example 1. In this experiment the incorporation of dATP[alpha-S] the gap-filling and the ligation step all take place at once.

1 mM $MgCl_2$, 20 mM 2-mercaptoethanol, 100 mg of bovine serum albumin per ml, 1.0 micromolar each of dATP[alpha-S], TTP[alpha-S], dATP and dTTP, and 100 picomoles of each of alpha-$^{32}$P-dATP and alpha-$^{32}$P-TTP (Specific activity 1000 cpm/picomole) are added to a 100 microliter buffer solution containing 50 mM Tris-HCl, pH 7.5.

To this solution are added a 5.0 microliter solution containing 100 picomoles of each of E and F' and each of phosphorylated F and E' and 0.1 picomole of 48 base pairs to be amplified. The resulting solution is heated to 100° C. for 3 minutes and allowed to cool to room temperature for 2 minutes, which allows the separation of the strands and hybridization of the set of two pairs to the target. Then 4 units of Klenow fragment of E. coli DNA polymerase-I and 2 units of T4-DNA ligase are added and the reaction incubated for 10 minutes at room temperature.

In order to cycle the process, the following steps are employed:
1. Heat for 3 minutes to 100° C.
2. Cool to room temperature for 2 minutes.
3. Add a mixture of 4 units of Klenow fragment of E. coli DNA polymerase-I and 2 units of T4-DNA ligase.
4. Incubate for 10 minutes at room temperature.

The cycle is repeated 22 times.

The resulting reaction mixture is loaded on a Sephadex G40/50 column (1×10 cm) (Pharmacia) and eluted with double distilled water. Two distinct peaks are separated and monitored by a Geiger counter. The first peak appearing after elution of 5–7 ml of water, consists of the amplified 48 base pairs and the second peak appearing, after elution of 14–18 ml of water, consists of alpha-$^{32}$P-dATP and alpha-$^{32}$P-TTP.

The following examples illustrate amplification use oligonucleotide complement pairs attached to photosensitive molecules.

EXAMPLE 5

Preparation of N-(2-bromoethyl) Phthalimide

Potassium phthalimide (30.8 g, 0.17 M) is stirred at room temperature for 48 hours with 1,2-dibromoethane (63.9 g, 0.34 M) and dry DMF (374 ml). (DMF is dimethyl formamide.) The precipitated KBr is filtered off, and the liquids are removed from the filtrate by distillation. The brown solid residue is recrystallized from cyclohexane-heptane (10:1) to give nearly colorless crystals (32.3 g, 72.3%, m.p. 73–75° C.).

EXAMPLE 6

Preparation of 8-hydroxypsoralen (Prepared By The Procedure Of A. Schonberg et al., J. Am. Chem. Soc., 72: 4826 (1950)).

A solution of 8-methylpsoralen (4.3 g, 19.90 mM) in dry benzene (100 ml) is added dropwise to magnesium iodide (from 10.16 g iodine and 0.97 g magnesium) in a mixture of dry ether (50 ml) and dry benzene (50 ml). The solvents are evaporated in vacuum at 120° C. until the residue is practically dry and then further heated at 160–170° C. for two hours.

The resulting solid residue is decomposed with dilute sulfuric acid and the filtered precipitate washed with water, suspended in dilute sodium bisulfite solution, filtered, washed with water and finally crystallized from dioxane as colorless crystals (m.p. 246° C.).

EXAMPLE 7
Preparation of 1-(Psoralen-8-yloxy)-2-N-phthalimidoethyl

To a stirred suspension of $K_2CO_3$ (5 g, 35 mM) in dry acetone (100 ml), 8-hydroxypsoralen (1 g, 5 mM) and N-(-2-bromoethyl) phthalimide (1.77 g, 7 mM) are added. The mixture is refluxed (17 hours) and, after cooling, filtered. After removal of the solvent, the crude product is chromatographed twice on silica gel (Hexane-Diethyl ether 1:1) resulting in the product becoming a yellow oil (6.68 g, 39%).

NMR ($DCl_3$) 3.31 (2H,t,J12 Hz,$CH_2N$); 4.75 (2H, t, J12 Hz, $CH_2O$), 6.38 (1H,d,J10 Hz,3-H), 6.82 (1H,d,J2 Hz,4-H), 7.40 (1H,S,5-H), 7.68 (1H,d,J2 Hz,5-H), 7.75 (4HJ,d, PHTHAL), 7.8 (1H,d,J10 Hz,4-H).

Mass spectrum, m/e 228, 229, 375($m^+$)

Anal. Calcd. for $C_{21}H_{13}NO_6$: C,67.2; H,3.4; N,3.7.
Found: C,67.0; H,3.4; N,3.6.

EXAMPLE 8
Preparation of 2-(8-psoralenoxy) Ethylamine Hydrochloride 1-(psoralen-8-yloxy)-2-N-phthalimidoethyl (0.5 g, 1.3 mM), hydrazine hydrate (85% in water, 0.5 ml), and 95% ethanol (100 ml) are refluxed for 4 hours, followed by a second 0.5 ml addition of the hydrazine hydrate solution. After extending the reflux for 2 hours, no starting material remained, as determined by thin layer chromatography (diethyl ether). The ethanol is evaporated and the residue is taken up in 200 ml of 0.1N NaOH, followed by extraction with three 50 ml portions of chloroform to give 135 mg (41.4%) of the crude amine. To prepare the hydrochloride, the amine is taken up in 100 ml of 1.2N HCl, which is extracted with three 30 ml portions of chloroform to remove impurities. Evaporation in vacuo of the acidic solution gave the crude hydrochloride, which is dissolved in enough absolute ethanol and precipitated by the addition of an equal volume of diethyl ether. After cooling overnight (4° C.), 98 mg of pure product is collected:

NMR ($CDCl_3$) as the amine 2.89 (2H,t,J9 Hz,$CH_2N$), 4.75 (2H,t,J9 Hz,$CH_2O$), 6.38 (1H,d,J10 Hz,3-H), 6.82 (1H,d,J10 Hz,4-H), 7.8 (1H, d, J10 Hz, 4-H) 7.9 (2H,wide,S,$NH_2$).

Mass spectrum m/e 201,245 ($M^+$).

Anal. Calcd. for $C_{13}H_{12}ClNO_4$: C,55.4; H,3.9. Cl,12; N,4.9;
Found: C,551; H,3.9; Cl,12.4; N,4.8.

EXAMPLE 9
Preparation Of The Photoactivable Groups Attached To Oligonucleotides The desired sequence to be amplified is a fifty base pair sequence contained within a plasmid pBR322 containing 8 kilobases of HIV genome as doubly stranded DNA. The sequence has the nucleotide sequence as follows:

5' CACTT TGGAAAGGAC CAGCAAAGCT CCTCTG-GAAA GGTGAAGGGG CAGTAG 4926-4976.

3' GTGAA ACCTTTCCTG GTCGTTTCGA GGAGAC-CTTT CCACTTCCCC GTCATC

See SEQ ID NO's. 11–12.

A. Synthesis of phosphorylated oligonucleotides.

The following four oligodeoxyribonucleotides are prepared by the phosphoramidite solid support of Matteuci et al., J. Am. Chem. Soc., 103: 3185 (1981).

Two of them, I and J', are phosphorylated at 5' end, whereas J and I' are phosphorylated at 3' end. The sequences of I, I', J and J' are as follows:

I—3'-GTGAAACCTTTCCTGGTCGTTTCGAG-P-5'
I'—5'-CACTTTGGAAAGGACCAGCAAAGCTC-P-3'
J—3'-P-GAGACCTTTCCACTTCCCCGTCATC-5'
J'—5'-P-CTCTGGAAAGGTGAAGGGGCAGTAG-3'

See SEQ ID NO's. 13–16.

In order to phosphorylate sequences I' and J at 3'-end, the following procedure is used.

30 mg of long chain alkylamine controlled pore glass (Pierce), pore diameter 500 Angstroms, particle size 125–177 mm, is placed in an appropriate cell that fits to Applied Biosystems Inc. type 380B-02 DNA synthesizer.

The procedure included condensation of the phosphorylating agent (2-cyanoethoxy)-2-(2'-0-4,4'-dimethoxytrityloxyethylsufonyl) ethoxy-N,N-diisoproplyamino-phosphine (Glen Corp. Inc.) followed by sequential condensation of diisoproplyphosphoramidite (Applied Biosystems Inc.).

Automated Synthesis Procedures:

The procedure included condensation of the phosphorylating agent with the long chain alkylamine controlled pore glass (CPG) using tetrazol as activating proton donor, and capping with acetic anhydride and dimethylaminopyridine in tetrahydrofuran and pyridine, detritylation using 2% trichloroacetic acid in dichloromethane, and oxidation of the phosphite to the phosphate with $I_2/H_2O$/lutidine/tetrahydrofuran. Cycle time is approximately 30 minutes.

The nucleotides of I' or J are sequentially condensed using the same cycle to the phosphorylating agent.

In order to synthesize 5'-phosphorylated oligonucleotides I and J', the cycle started with detritylation of the derivatized controlled pore glass with the appropriate nucleotides following the cycle steps as described above. In the last cycle, the phosphorylating agent is condensed. Yields at each step are essentially quantitative and are determined by collection and spectroscopic examination of the dimethoxytrityl alcohol released during detritylation.

Oligodeoxyribonucleotide Deprotection and Purification Procedures:

The solid support is removed from the column and exposed to 1 ml concentrated ammonium hydroxide at 60° C. for 16 hours in a closed tube. Ammonia is removed and the residue is applied to a preparative 12% polyacrylamide gel using a Tris-borate buffer (pH 8) containing 7M urea. Electrophoresis is carried out at 20 volts/cm for 5 hours after which the band containing the product is identified by UV shadowing of a fluorescent plate. The band is excised and eluted with 1 ml distilled water overnight at room temperature. This solution is filtered and the supernatant is extracted (3×300 microliter) with n-butanol. The water phase is placed on a Sephadex G50 column (Pharmacia)(1×10 cm) and eluted with double distilled water. The elution is monitored by UV absorbance at 260 nm and the appropriate fraction collected, quantitated by UV absorbance in a fixed volume and evaporated to dryness at room temperature in a vacuum centrifuge.

Kination of I' and J segments:

The oligodeoxyribonucleotides I' and J (5 nanomoles each) are lyophilized separately to dryness and redissolved in (50 microliter) of 50 mM of HEPES (Aldrich) pH 7.6, 10 mM $MgCl_2$, 10 mM dithiotreitol and [alpha-$^{32}$P]-ATP (10 nM) specific activity=2.5×10$^3$ CPM/pmole.

Each tube is incubated with two units of T4-polynucleotide kinase for 40 minutes at 37° C. for five minutes to inactivate the enzyme, and are loaded on sephadex columns G50 and eluted with water. The elutions are monitored by Geiger counter (Beckman) and lyophilized to dryness.

EXAMPLE 10
Preparation Of Photoactivable-oligodeoxyribonucleotides

This example illustrates the labeling of any oligonucleotide with photoactivable group at 3' or 5' ends. In this example, x=y=any amino photoactivable group, such as 2-(8-psoralenoxy) ethylamine as described above in this invention or 5-aminomethyl-8-methoxypsoralen as described by J. B. Hansen et al., Tetrahedron Letters, 22: 1847–48 (1981), or 4'-aminomethyl-4-5; 8-trimethylpsoralen as described by Isaacs et al., Biochemistry, 16: 1058–64 (1977).

Phosphorylated oligodeoxyribonucleotides, 5'PI, 3'PJ, 3'PI' and 5'PJ' (10 nmoles) each are lyophilized separately to dryness in an Eppendorf tube. A solution of 0.2 M 1-Ethyl-3,3-dimethylaminopropylcarbodiimide (Sigma), (8-Psoralenoxy) ethylamine. Hydrochloride (10 mg) and 0.1 M of 1-methylimidazole buffer at pH 6.0 (1 ml) is made. 250 microliters from this solution is added to each of the Eppendorf tubes.

The mixtures are incubated for 24 hours at room temperature. The tubes are evaporated to dryness, the residues are redissolved in 30 microliters of 8% formamide and are purified by preparative electrophoresis on 12% polyacrylamide gels using a Tris-borate buffer pH 8 containing 7M urea. Electrophoresis is carried at 20 volts/cm for 3 hours after which the band containing the product is identified by U.V. shadowing of a fluorescent plate. Two bands are identified that ran closely, the upper band showed a fluorescence upon exposure to long wave U.V. lamp.

The bands are excised and eluted with 1 ml distilled water overnight at room temperature. The mixtures are filtered and the supernatants are extracted (3×0.5 ml) with n-butanol. The aqueous phases are loaded on a Sephadex G50 column and eluted with water. The elution is monitored by U.V. absorbance at 260 nm and at 310 nm, and the appropriate fractions are collected, quantitated by U.V. absorbance in a fixed volume and evaporated to dryness at room temperature in a vacuum centrifuge. The yield of the photolabeling is 85%.

Radiolabeling of yI' and yJ at the 5' ends.

5 nanomoles each of lyophilized yI' and yJ are dissolved (50 microliters) in 5 nM of HEPES pH 7.6, 10 mM $MgCl_2$, 10 mM dithiothreiteol and [$^{32}$P]-ATP (10 nM, specific activity=2.5×10$^3$ CPM/Pmole) and incubated with 1 unit of T4-polynucleotide kinase for 40 minutes at 37° C. The reaction mixtures are warmed to 80° C. for 5 minutes to inactivate the enzyme. The content of each tube is loaded on a Sephadex G50 column (1×10 cm) and eluted with double distilled water.

The elution is monitored by Geiger counter and the appropriate fraction is collected, quantitated by radioactivity counting in a fixed volume and evaporated to dryness at room temperature in a vacuum centrifuge.

EXAMPLE 11

This example illustrates amplification of a 51 base pair sequence of HIV genome contained within the plasmid pBR322 using the photochemical process according to this embodiment of the invention.

The plasmid contains 8 kilobases of human immunodeficiency veins HIV genome sequence in which 51 base pairs are selected to be amplified from the POL region.

A total of 10 picomoles of the plasmid is linearized with EcoRI. One nanomole each of the following photoactivable-oligodeoxyribonucleotodes are designed to produce a photoproduct adduct of 51 bases in length when I and J or I' and J' are joined together:

Ix=3'-GTGAAACCTTTCCTGGTCGTTTCGAG-P-x-5'
I'y=5'-*PCACTTTGGAAAGGACCAGCAAAGCTC-P-y-3'
Jy=3'-y-P-GAGACCTTTcCACTTCCCCGTCATCP*-5'
J'x=5'-x-P-CTCTGGAAAGGTGAAGGGGCAGTAG-3'

See SEQ ID NO's. 17–20.
where x=y=2-(8-psoraleneoxy)ethylamino and p* is the radioactive labeled phosphorus.

Sequences yI' and yJ are kinased at 5' end as described above. The radioactive labeled sequences are used for the analysis of the amplification efficiency when using the process and are dissolved in 100 ml of 1M guanine thiocyanate (GUSCN) solution.

The mixture is placed in a siliconized 1.5 ml polypropylene centrifuge tube (Sarstedt) and is flushed by bubbling the mixture with nitrogen for five minutes. The mixture is immersed in a 100° C. water bath for two minutes, followed by quick cooling to 37° C. and a five minute irradiation period. The cycle of heating, cooling and irradiating is repeated seven times.

The irradiation step is undertaken in an apparatus containing two 400-W General Electric mercury-vapor lamps (H400 A 33-1/T16), which are mounted on either side of a double-walled sample chamber, at a distance between centers of nine cm. The sample holder is maintained at 37° C. by a thermostat and shielded by $Co(NO_3)_2$/NaCl/$H_2O$ mixture (38:2:60 by weight) and with a 0.6 cm pyres filter. The cobalt solution served as an ultraviolet filter, which allowed a maximum transmittance of 365 nm light and a window from approximately 340–380 nm. The intensity of the light at the surface of the inner sample is approximately 100 mW/cm2.

After each irradiation, an aliquot of 5 ml is removed and kept for analysis.

After the seventh cycle, the aliquots are loaded on a 12% polyacrylamide gel using a Tris-borate buffer, pH 8 containing 7M urea. Electrophoresis is carried out at 20 volt/cm form three hours. The gel is exposed to a film for four hours.

EXAMPLE 12

This example illustrates the coupling of T4-DNA ligase and Polymerase-I to polymeric supports.
I. Synthesis of the "linker arm".
1. O-(di-p-methoxytrityl)hexaethylene glycol. Hexaethylene glycol (Aldrich), (28.23 g, 100 mmole) is dissolved in dry pyridine (200 ml) and a solution of dimethoxytrityl chloride (16.95 g, 50 mmole) in dry pyridine (100 ml) is added dropwise under argon. The mixture is stirred at room temperature for 4 hours and the solvent is removed under reduced pressure (2 mm Hg). The oily yellow residue is extracted with ethyl acetate (300 ml) and washed with water (200 ml) and brine (2×200 ml). The organic layer is dried over anhydrous sodium sulfate and filtered. The solvent is removed and the residue is redissolved in dichloromethane (30 ml) which contains some pyridine (0.5 ml). This mixture is further purified by column chromatography on silica gel (5.5×45 cm) and eluted with a mixture of dichloromethanemethanol-pyridine (95:4:1: vol/vol). The product (23.3 g, yellow oil) has a RF=0.42 in the above solvents. The yield is (80%).

NMR=7.46–7.20 (m, 9H, aromatic Hs), 6.80 (d, J=9.0 Hz, 4H, aromatic Hs), 3.77 (s, 6H, methoxy Hs), 3.66, 3.63 (2s, 22H, $CH_2$—$CH_2$) 3.56 (t, J=5 Hz, sH, $CH_2$—OH), 3.21 (t, J=6.0 Hz, 2H, $CH_2$-DMT), 2.49 (wide s, 1H, OH). Mass spectrum: m/e 584 (molecular ion), 553, 507, 477, 303 (DMT group).

2. O'-DMT-hexaethyleneglycol O-Methyl N,N-diisopropyl phosphoramidite.

O'-DMT-hexaethyleneglycol (1) (5.84 g, 10 mmole) is dissolved in dry dichloromethane (30 ml) under argon. Dry N,N-di-isopropylethyl amine (5.16 g, 40 mmole) is added followed by dropwise addition of N,N-di-isopropyl O-methyl chlorophosphoramidite (Applied Biosystems) (1.97 g, 10 mmole). The solution is stirred at room temperature for 30 minutes, diluted with ethyl acetate (300 ml), washed with a saturated solution of sodium bicarbonate (100 ml) and with brine (100 ml). The organic layer is dried over anhydrous sodium sulfate and the solvent is removed under reduced pressure (15 mm Hg). Further drying is achieved by coevaporation with toluene (2×100 ml) and by lyophilization in dry benzene.

The product (7.21 g, yellow oil) has RF-0.63 in dichloromethane-methanol (95:5). The yield is (95%). NMR =7.47–7.23 (m, 9H, aromatic Hs), 6.83 (d, J=9.0 Hz, 4H, aromatic Hs), 3.77 (s, 6H, methoxy), 3.77–3.59 (wide s, 22H, O—$CH_2CH_2$—O), 3.55 (d, J-12 Hz, 3H, $CH_3$—O—P), 3.21 (t, J=6.0 Hz, 2H, $CH_2$—O-DMT), 1.62 (d, 2H, $CH_3$—CH), 1.24 (d, J=7 Hz, 12H). Mass spectrum 744 (molecular ion).

II. Attachment of the linker-arm to controlled pore glass.

1 gram of long chain alkyl amine-controlled pore glass (CPG), (Pierce), (500 Angstrom pore diameter), is placed in a sinter glass (medium) (50 ml), and washed with dry acetonitrile (3×10 ml) under argon. To the dried gel, a solution of 1H-Tetrazole (Aldrich), (0.5 g) in dry acetonitrile (12 ml), is added, followed by addition of a solution of O'-DMT-hexaethyleneglycol O-methyl N, N-diisopropyl phosphoramidite (2 g) in dry acetonitrile (13 ml), under argon. The reaction mixture is agitated for 10 minutes followed by washings with tetrahydrofuran (3×25 ml). To the resulting gel, a capping solution containing acetic anhydride:tetrahydrofuran (1:1 vol/vol) (10 ml), and a solution of N,N-dimethylamino pyridine (0.5 g) in tetrahydrofuran (10 ml) are added, and the mixture is shaken for 6 minutes, followed by washings with tetrahydrofuran (3×20 ml). To the resulting solution an oxidation solution containing I2 (0.1 Molar) in tetrahydrofuran:water: 2,6-lutidine (1:0.4:1), (10 ml) is added, and the mixture is shaken for 5 minutes, followed by washings with acetonitrile (3×20 ml). The measurement of the loading of the linker-arm on the controlled pore glass is done by adding a solution (1 ml) of para-toluenesulfonic acid in acetonitrile (0.1 Molar), to a 10 milligram of the derivative support, followed by measuring the absorbance at 498 nm. The loading is 185 micromoles of the linker-arm per 1 gram of the support. The dimethoxytrityl group is removed from the support, by a solution of trichloroacetic acid in dichloromethane (3%). A new linker-arm could be condensed to the previous unprotected linker-arm in order to obtain a longer linker-arm, as desired.

III. Activation of the CPG-linker-arm with tresyl chloride.

The dried support-linker-arm (1 g), is placed in a sinter glass as above, and washed with dry acetone (3×50 ml), followed by addition of dry acetone (5 ml) and 260 microliters of dry pyridine. Tresyl chloride (Fluka), (180 microliters) is added to the suspension dropwise for 1 minute, under shaking. After reaction for 15 minutes at 0° C., the gel is washed twice with (20 ml) of the following, 30:70, 50:50, and 70:30 of 5 mM HCl:acetone (vol/vol) and finally with water, 50:50 water:acetone and acetone, (20 ml each) dried, and stored in desiccator until required.

IV. Coupling of T4-DNA Ligase to tresylated CPG-linker-arm.

40 units of T4-DNA ligase (BRL), are dissolved in 0.1 M $NaH_2PO_4$, pH7.5, containing 1 mM EDTA, 50 micromolar ATP, 10% glycerol to a final volume of 200 microliters and kept at 40° C. 100 milligrams of dry tresylated CPG-linker-arm is transferred to the enzyme solution. The resulting gel slurry is mixed "end over end" at 4° C. for 16 hours. Residual reactive tresyl groups on the linker-arm are removed by adding 0.1M dithiotreitol, (2 hours, 4° C.). After coupling, the gel is washed free of uncoupled enzyme by washing four times in 0.1M $NaH_2PO_4$, pH 7.5, 1 mM EDTA, 10 mM dithiothreitol (DTT), 0.5 M NaCl followed by two washes in 0.1M NaAc, pH 5.0. Finally, the gel is equilibrated in 66 mM Tris-HCl, pH 7.6, 6.6 mM $MgCl_2$, 10 mM DTT, 10% glycerol and stored at 4° C.

V. Coupling of Klenow fragment of *E. coli* DNA Polymerase-I to tresylated CPG-linker-arm.

40 units of Klenow fragment of *E. coli* DNA Polymerase-I (Bethesda Research Labs.) are dissolved in 200 microliters of buffer consisting of 1.5 mM ATP; 30 mM Tris acetate buffer at pH 7.9; 60 mM sodium acetate; 10 mM magnesium acetate; and added to a lyophilized mixture of 80 microgram Poly (dA)-20 microgram oligo (dT). To this mixture is added 100 milligrams of dry tresylated CPG-linker-arm. The resulting gel slurry is mixed "end-over-end" at 4° C. for 10 hours. Residual reactive tresyl groups on the linker-arm are removed by adding 0.1 mM dithiothreitol (DTT), (2 hours, 4° C.). After coupling, the gel is washed free of uncoupled enzyme by washing (4×0.5 ml) in a buffer consisting of 60 mM sodium acetate, 30 mm Tris acetate, 10 mM magnesium acetate at pH 8.0 and 0.25 mM dithiotreitol. Finally, the gel is equilibrated in 66 mM Tris-HCl pH 7.6; 6.6 mM magnesium chloride; 10 mM DTT; 10% glycerol and stored at 4° C.

The following examples illustrate the use of these immobilized enzymes in the method of the application.

EXAMPLE 13

Step 1: The synthesis of the Chlamydia sequence.

The desired sequence to be amplified using the gap-filling/ligating system of joining the oligonucleotides has 88 base pairs that code for Chlamydia trachomatis cryptic plasmid. This particular sequence is a quadruple repeat sequence of 22 base pairs obtained by sequencing the 6.5 kilobase plasmid derived from Chlamydia trachomatis (serotype L) inserted into the unique Bam H1/SSt1 sites of the PUC18 plasmid. The 6.5 Kb are sequenced using the dideoxy chain termination method of Sanger et al. Proc. Natl. Acad. Sci. 83, 1911 (1986).

The 22 repeated base pair has the following sequence:
5'-(GTCTACCACCAAGAGTTGCAAA)x4-3'
3'-(CAGATGGTGGTTCTCAACGTTT)x4-5'
See SEQ ID NO's. 21–22.

The construction of the two pairs is as follows:
Y=5'-AGTCTACCACCAAGAGTTGC-3'
Z=3'-CAGATGGTGGTTCTCAACGT-5'
See SEQ ID NO's. 23–24.

Y represents in this case oligonucleotides A and B in the oligonucleotide complement pairs.

Z represents in this case oligonucleotides A' and B' in the oligonucleotide complement pairs. When hybridized to the target sequence, Y and Z form a gap of two complementary base pairs, A–T.

The two oligodeoxyribonucleotides described above are synthesized and purified by the following procedure.

I. Automated Synthesis Procedures. (according to Matteucci et al., J. Am. Chem. oc., 103, 31–5, (1981).

The 2-cyanoethyl phosphoramidites are purchased from Applied Biosystems Inc. The procedure includes condensation of nucleoside phosphoramidites to 30 mg of a nucleoside-derivatized controlled pore glass (CPG) bead support, (500 Angstrom pore diameter), using a DNA synthesizer from Applied Biosystems Inc., Type 380B-02. The cycles includes detritylation with 2% trichloroacetic acid in dichloromethane; condensation using tetrazole as an activating proton donor; capping with acetic anhydride and dimethylaminopyridine; detritylation using 2% trichloroacetic acid in dichloromethane; and oxidation of the phosphite to the phosphate with 0.1 M $I_2/H_2O$/lutidine/tetrahydrofuran. Cycle time is approximately 30 minutes. Yields at each step are essentially quantitative and are determined by collection and spectroscopic examination of the dimethoxytrityl alcohol released during detritylation.

II. Oligodeoxyribonucleotide Deprotection and Purification Procedures.

The solid support is removed from the column and exposed to 1 ml concentrated ammonium hydroxide at 60° C. for 16 hours in a closed tube. Ammonia is removed and the residue is applied to a preparative 12% polyacrylamide gel using a Tris-borate buffer (pH 8) containing 7M urea. Electrophoresis is carried out at 20 volts/cm for 5 hours after which the band containing the product is identified by UV shadowing of a fluorescent plate. The band is excised and eluted with 1 ml double distilled water overnight at room temperature. This solution is filtered and the supernatant is extracted (3×300 microliter) with n-butanol. The water phase is placed on a Sephadex G-50 column (Pharmacia) (1×10 cm). The elutions are monitored by UV absorbance at 260 nm and the appropriate fraction collected, quantitated by UV absorbance in a fixed volume and evaporated to dryness at room temperature in a vacuum centrifuge.

III. 5'-Phosphorylation of A, B, A' and B'.

The oligodeoxyribonucleotides Y and Z (5 nanomoles each) are lyophilized separately to dryness and redissolved in (50 microliter) of 50 nM HEPES (Aldrich) pH 7.6, 10 nM, $MgCl_2$, 10 mM dithiotreitol and [alpha-$^{32}$P]-ATP (10 nM). Specific activity=$2.5\times10^3$ cpm/pmole.

Each tube is incubated with two units of T4 polynucleotide kinase for 40 minutes at 37° C. for five minutes to inactivate the enzyme, and are loaded on Sephadex columns G50 and eluted with water. The elutions are monitored by gamma counter (Beckman) and lyophilized to dryness.

EXAMPLE 14

I. Purification of Chlamydial DNA

Chlamydia trachomatis LGV2 strain is grown in McCoy cells in the presence of 1 microgram cycloheximide/ml until about 1.0 IFU (inclusion-forming unit) per cell. The cells are grown for 3 days at which time 80–90% of them showed visible inclusions and are harvested and stored at −70° C. until tested. Control microbial strains are obtained from routine isolations (Department of Microbiology, Ben-Gurion University) and identified by standard procedures (Lennette et al., Manual of Clinical Microbiology, 3rd edition, Washington (1980)). The strains include isolates of E. coli and Streptococcus agalactiae.

The microbial strains are grown on plates or in liquid medium. For the test, a suspension of each of the microbes is boiled at an alkaline pH (0.3 M NaOH), chilled on ice and neutralized with HCl.

The Chlamydial cell culture harvests of 100 ml are disrupted with a glass-Teflon homogenizer and centrifuged at 1.400× g for 5 minutes to remove cell debris. The supernatant is layered onto 30% (vol/vol) Renografin −76 (E. R. Squibb, Princeton U.S.A.) diluted with 20 mM Tris-150 mM HCl (THCl) (pH 7.5); Renografin 76, (a solution of diatrizoate meglumine and diatrizoate sodium in citrate buffer).

After centrifugation at 50,000× g for 45 minutes, the pellets are resuspended in 1.0 ml of THCl, layered onto 30 to 60% (vol/vol), Renografin −76 gradients in THCl, and centrifuged at 50,000× g for 2 hr.

Two diffuse bands are visible in the middle region of the gradient; these fractions are collected, diluted with THCl and centrifuged at 50,000× g for 45 min. The pellets are resuspended in 0.5 ml of THCl.

II. DNA Extraction

The following procedure is based on the method described by (Wenman et al., Nature 296:68–70 (1982)).

The Chlamydial suspension is homogenized before the addition of 50 mM Tris containing 20 mM $Na_2$EDTA 20% (wt/vol) sucrose, 0.7% (wt/vol) N-lauroylsarcosine; and 200 micrograms of proteinase K. This mixture is incubated at 55° C. for 15 min. and then at 37° C. for 45 min. An equal volume of phenol-chloroform is added and the mixture is vortexed and centrifuged at 2,000× g for 10 min. Nucleic acids are precipitated from the aqueous phase by addition of a ¹⁄₂₀ volume of 5M NaCl and 2 volumes of ethanol. After two further cycles of centrifugation and precipitation, the DNA is measured spectrophotometrically, precipitated once more, and redissolved in 10 mM Tris with 1 mM EDTA (pH 7.0) at a concentration of 200 microgram/ml.

DNA is digested in 4 to 10 microgram amounts at a concentration of 80 microgram/ml with 4 units of BAMH1 (B1) per microgram of DNA for 2 to 3 hours, under the conditions recommended by the manufacturer.

EXAMPLE 15

This example illustrates the gap filling-ligation amplification steps using immobilized enzymes.

A mixture of polymeric beads, (10 mg beads) of CPG-T4-DNA ligase from Example 12. IV and (10 mg beads) of CPG-Klenow fragment of E. coli. DNA Polymerase-I from Example 12.V, are placed in plastic cylinder (inner volume= 0.5 ml), where the edges of the cylinder contain plastic covers a, b, having an inlet and an outlet that connect to plastic tubing. The bottom of the cylinder is filled with siliconized glass wool, which holds the beads.

The inlet and outlet are attached to plastic tubing that has a diameter of 0.5 mm. The plastic tubing is attached to stainless steel coil, which is immersed in a hot oil bath, containing silicon oil at 90° C. The stainless steel coil is attached by a tube to second stainless coil. The second coil is immersed in a water bath and held at room temperature. Both coils are also 0.5 mm in diameter. The second coil is attached to plastic tube having a diameter of 0.5 mm. The tube is connected to peristaltic pump and thereafter to the cell through the inlet. The pump pushes the solution through the system at a rate of two drops per minute.

Step 1. Protection of Y and Z Oligonucleotides from the 3'-5' Exonuclease Activity of DNA Polymerase I and to Form Blunt Ends. 100 picomole of each 5'-phosphorylated Y and Z are mixed together and dissolved in 1 milliliter of 1 MM $MgCl_2$, 20 mM 2-mercaptoethanol, 100 mg of bovine serum albumin per ml and 50 mM Tris-HCl (pH 7.5), and 0.1 mM of dATP[alpha-S] and TTP[alpha-S] (Sigma).

The resulting solution is heated to 100° C. for 2 minutes which allows separation of the strands and hybridization of the Y and Z to the target. Then 5 units of Klenow fragment of E. coli DNA polymerase-I are added and the reaction is incubated for 10 minutes at room temperature. The pairs are now blunt-ended and protected against exonuclease activity of polymerase.

Step 2. 1 microgram of Bam HI digested DNA from Example 14.II above is dissolved in the buffer resulted from step 1. To this buffer is added 1 nanomole of dATP and TTP and 100 pmoles of each of alpha-$^{32}$P [dATP] and alpha-$^{32}$P [TTP]. Specific activity 1000 cpm/picamole.

This solution is injected through the inlet of the apparatus and the cycling is started by operating the peristaltic pump.

After 3 hours of cycling the solution through the cell containing the immobilized enzymes, the solution is loaded on a Sephadex column G-40/50 (1×10 cm) and eluted with doubly distilled water. Fractions of 1 ml are collected and monitored by a Geiger counter.

Two distinct bands are detected, the first is eluted in a pool of 4–7 ml containing labeled amplified joined oligonucleotide products by gap filling/ligation process. This pool has about 115,000 cpm whereas the second pool that eluted in 14–17 ml has 80,000 cpm.

EXAMPLE 16

This example illustrates the synthesis of complementary oligonucleotide pairs for use in amplifying and detecting nucleic acid sequences from Chlamydia trachomatis. The desired sequence to be amplified is a 50 base pair sequence (nucleotides 6503–6552) contained in the double stranded Chlamydia trachomatis cryptic plasmid pLGV440, as published by C. Hatt et al. in Nucleic Acids Research 16:4053–4067 (1988).

The target sequence has the nucleotide sequence as follows:

```
                        TARGET CH (+)
5' - TTTTGGCCGCTAGAAAAGGCGATTTAAAAACCAAGGTCGATGTGATAGGG - 3'
3' - AAAACCGGCGATCTTTTCCGCTAAATTTTTGGTTCCAGCTACACTATCCC - 5'
                        TARGET CH (-)
```

See SEQ ID NO's. 25–26.

The gaps formed when the respective oligonucleotide pairs are hybridized to each of the target sequences are underlined above.

When the oligonucleotide pairs CH1, CH5, CH2', CH4' are hybridized to the target sequence, a gap exists between each pair as illustrated:

```
                                                    Target (+)
5' - --------------------ATTTAA---------------------- - 3'
     --------------------       ----------------------
           CH5                         CH1

CH2'                        CH4'
     --------------------       ----------------------
3' - --------------------ATTTT---------------------- - 5'
                                                    Target (-)
```

I. Synthesis of the oligonucleotide pairs that when hybridized to the target sequences will form the gaps identified above.

The two oligonucleotide pairs are designed as follows:

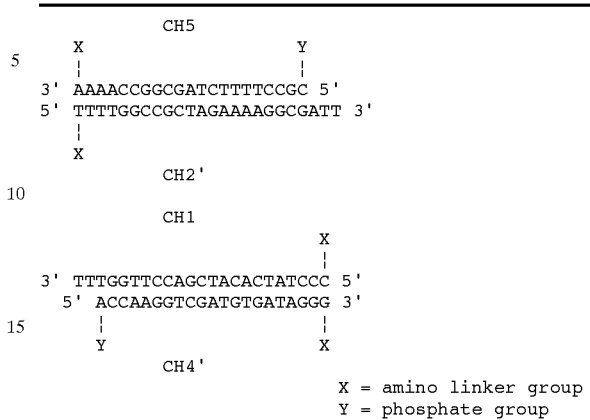

See SEQ ID NO's. 27–30.

II. Automated Synthesis Procedures. (according to Matteucci et al., J. Am. Chem. oc., 103, 31–5, (1981).

The 2-cyanoethyl phosphoramidites are purchased from Applied Biosystems Inc. The procedure includes condensation of nucleoside phosphoramidites to 30 mg of a nucleoside-derivatized controlled pore glass (CPG) bead support (127–177 mm particle size, 500 Angstrom pore diameter) using a DNA synthesizer from Applied Biosystems Inc., Type 380B-02. The cycles includes detritylation with 2% trichloroacetic acid in dichloromethane; condensation using tetrazole as an activating proton donor; capping with acetic anhydride and dimethylaminopyridine; detritylation using 2% trichloroacetic acid in dichloromethane; and oxidation of the phosphite to the phosphate with 0.1 M $I_2/H_2O$/lutidine/tetrahydrofuran. Cycle time is approximately 30 minutes. Yields at each step are essentially quantitative and is determined by collection and spectroscopic examination of the dimethoxytrityl alcohol released during detritylation.

The oligonucleotides CH1 and CH2' are derivatized at their 5' ends with an amino linker arm using 6-(trifluoroacetylamine)-hexyl-(2-cyanoethyl)-(N,N-diisopropyl) phosphoramidite (Glen Research Corp.). This reagent is condensed to the 5' end —OH— of the oligonucleotides CH1 and CH2' in the last cycle using the cycling as above.

Oligonucleotides CH4' and CH5 are derivatized at their 3' ends with an amino linker arm by starting their synthesis with derivatized controlled pore glass (CPG) bead support using (1-Dimethyloxytrityloxy-3-fluorenylmethoxycarbonylamino-propan-1-succinoyl)— long chain alkylamino -CPG (Glen Research Corp.) using the cycle of synthesis as described above.

5'-phosphorylation of oligonucleotides CH4' and CH5 is performed by condensing the 5'-phosphorylating reagent 2-[2-(4,4'-dimethyoxytrityloxy) ethyl sulfonyl] ethyl-(2-ganoethyl)-(N,N-diisopropyl)-phosphoramidite as described by T. Horn et al., in Tetrahedron Letters 27: 4705–4708 (1986) and purchased from Glen Research Corp.

This phosphorylating reagent is condensed to the 5' end of the oligonucleotides CH4' and CH5 using tetrazol as an activating proton donor, followed by capping with acetic anhydride and dimethylaminopyridine; detritylation with 2% trichloroacetic acid in dichloromethane; and oxidation of the phosphite to the phosphate with 0.1 M $_2$/H$_2$O/lutidine/tetrahydrofuran.

III. Oligodeoxyribonucleotide Deprotection and Purification Procedure.

The solid support is removed from the column and exposed to 1 ml concentrated ammonium hydroxide at 60° C. for 16 hours in a closed tube. Ammonia is removed and the residue is applied to a preparative 12% polyacrylamide gel using a Tris-borate buffer (pH 8) containing 7M urea. Electrophoresis is carried out at 20 volts/cm for 5 hours after which the band containing the product is identified by UV shadowing of a fluorescent plate. The band is excised and eluted with 1 ml double distilled water overnight at room temperature. This solution is filtered and the supernatant is extracted (3×300 microliter) with n-butanol. The water phase is placed on a Sephadex G-50 column (Pharmacia) (1×10 cm). The elutions are monitored by UV absorbance at 260 nm and the appropriate fraction collected, quantitated by UV absorbance in a fixed volume and evaporated to dryness at room temperature in a vacuum centrifuge.

EXAMPLE 17

This example illustrates the gap-filling/ligation embodiment to amplify and detect a pair of complementary synthetic oligonucleotide target sequences derived from the cryptic plasmid of Chlamydia trachomatis described in example 16. The oligonucleotide probes CH1, CH4'; CH5, CH2' described in example 16 are used in this procedure to amplify the target sequences.

I. Procedure

Materials:

Each 50 ul aliquot of reaction mixture contains the following:
- 350 ng of each of the four synthetic oligonucleotide probes-CH1, CH4'; CH5, CH2' (from example 16).
- 250 ng of human placenta DNA (Sigma).
- 10 uCi $^{32}$P-dATP.
- 50 units of heat stable ligase (Epicenter).
- 2.5 units of Taq polymerase (Perkin Elmer).
- in: 20 mM Tris-HCl pH 7.6, 10 mM MgAc, 25 mM KAc, 0.6 mM NAD, 10 mM DTT, 0.2 mM dATP and 0.2 mM of dTTP.

Methods:

50 ul of reaction mixture is added to each of 6 microfuge tubes (500 ul size).

To the first tube is added 1 ul of a sample (negative control) containing 40 ng of human placenta DNA in 1 ul distilled water (dH$_2$O).

To each successive tube is added 1 ul of a serial dilution of the double stranded synthetic Chlamydia trachomatis oligonucleotide target sequences as follows:

| Tube | Amount of CH +/- Target (picograms) |
|------|-------------------------------------|
| 1    | Control, no target                  |
| 2    | 2,000                               |
| 3    | 40                                  |
| 4    | 0.8                                 |
| 5    | 0.016                               |
| 6    | 0.00032                             |

Each of the tubes is covered with 50 ul of light mineral oil to prevent evaporation.

The six tubes are placed in a DNA Thermal Cycler (Perkin Elmer Model 4800). The cycler is programmed as follows:

Initial Denaturation at 94° C. for one minute.

30 cycles of 90° C. for one minute and 45° C. for five minutes.

After the cycling is completed, 50 ul of dye solution containing 30% glycerol in water and 0.1% bromophenol blue is added to each of the six tubes.

Twenty microliters of solution from each tube is loaded on a 12% polyacrylamide gel using Tris-borate buffer (pH 8). Electrophoresis is carried out at 20 volts/cm for three hours, after which the gel is exposed to a Kodak X-OMAT AR film for three hours.

EXAMPLE 18

This example illustrates the gap filling-ligation embodiment to amplify and detect the Chlamydia trachomatis cryptic plasmid DNA sequences described in example 16. The oligonucleotide probes CH1, CH4'; CH5, CH2' described in example 16 are used in this procedure to amplify the target sequences.

Chlamydia trachomatis L2/LGV-434 genomic DNA containing the cryptic plasmid is isolated from L-929 mouse fibroblast cells (ATCC CCL1-NCTC Clone 929) grown in suspension culture, 24 hours after infecting with C. trachomatis L2.

I. Procedure

Materials:

Each 50 ul aliquot of reaction mixture contains the following:
- 350 ng of each of the four synthetic oligonucleotide probes; CH1, CH4'; CH5, CH2' (from example 16).
- 250 ng of human placenta DNA (Sigma).
- 10 UCi $^{32}$P-dATP.
- 50 units of heat stable ligase (Epicenter).
- 2.5 units of Taq polymerase (Perkin Elmer).
- in: 20 mM Tris-HCl pH 7.6, 10 mM MgAc, 25 mM KAc, 0.6 MM NAD, 10 mM DTT, 0.2 mM dATP and 0.2 mM of dTTP.

Methods:

50 ul of reaction mixture is added to each of 6 microfuge tubes (500 ul size).

To the first tube is added 1 ul of a sample (negative control) containing 40 ng of human placenta DNA in 1 ul distilled water (dH$_2$O).

To each successive tube is added 1 ul of a serial dilution of C. trachomatis L2/LGV-434 DNA target sequences as follows:

| Tube | Amount of CH +/− Target (picograms) |
|---|---|
| 1 | Control, no target |
| 2 | 2,000 |
| 3 | 80 |
| 4 | 8 |
| 5 | 0.8 |
| 6 | 0.08 |

Each of the tubes are covered with 50 ul of light mineral oil to prevent evaporation.

The six tubes are placed in a DNA Thermal Cycler (Perkin Elmer Model 4800). The cycler is programmed as follows:

Initial Denaturation at 94° C. for one minute.

30 cycles of 90° C. for one minute and 45° C. for five minutes.

After the cycling is completed, 50 ul of dye solution containing 30% glycerol in water and 0.1% bromophenol blue is added to each of the six tubes.

Twenty microliters of solution from each tube is loaded on a 12% polyacrylamide gel using Tris-borate buffer (pH 8). Electrophoresis is carried out at 20 volts/cm for three hours, after which the gel is exposed to a Kodak X-OMAT AR film for three hours.

EXAMPLE 19

This example illustrates the amplification and detection of Human Papilloma Virus 16 (HPV16) DNA in a Ca Ski Cell line and in clinical cervical biopsy samples using the gap filling-ligation embodiment. The HPV16 target DNA sequence spans bases 6631–6687 from the putative L1 peptide encoding region of the genome having the sequence:

5'     C T G T T G T T G A T A C T A C A C G C A G T A-
CAAATATGTCATTATGTGCTGCCATATCTACTT 3'

3'   G A C A A C A A C T A T G A T G T G C G T C A T G T T-
TATACAGTAATACACGACGGTATAGATGAA 5'

See SEQ ID NO's. 31–32.

The gaps formed when the respective oligonucleotide pairs are hybridized to each of the target sequences are underlined above.

In each of the complementary oligonucleotide pairs, there are 5' overhung bases. The 5' and 3' ends are protected with an amino linker arm, which is useful in non-radioactive labeling. The construction of the oligonucleotides is as follows:

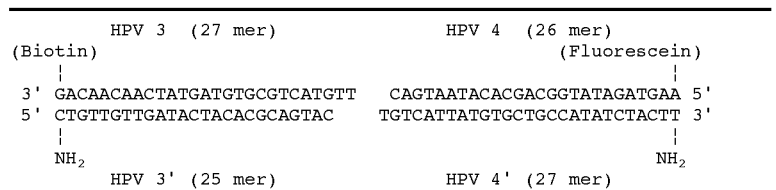

See SEQ ID NO's. 33–36 (HPV 4, HPV 3, HPV 3' and HPV 4' respectively).

When these oligonucleotide pairs are hybridized to the HPV16 target sequence, a gap exists between each pair as illustrated:

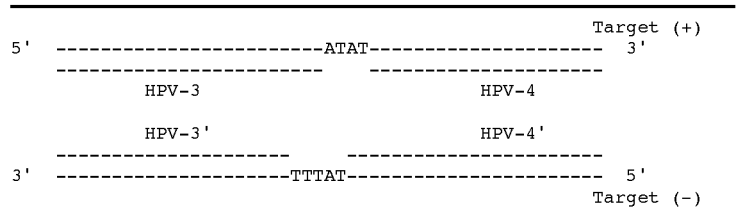

I. Preparation of Biopsy Samples for Detection of Target Sequences.

Three clinical cervical biopsy samples are treated with a solution of 11 ul of 10 mg/ml Proteinase K (Boehringer Mannheim) for two hours at 64° C., and then are boiled for 10 minutes. The target solutions are treated twice with phenol/chloroform (1:1), and once with chloroform. The nucleic acids in the water phase are precipitated by ethanol and quantitated by their absorption at 260 nm. The total nucleic acid concentrations of each sample are as follows:

Biopsy #41—92 ng/ul

Biopsy #63—222 ng/ul

Biopsy #59—93 ng/ul

II. Preparation of Caski Cell Line Target Sequences for use as a Positive Control.

A sample of DNA from a Ca Ski target cell line (ATCC CRL 1550) is obtained by treating the cells with a solution of 11 ul of 10 mg/ml Proteinase K (Boehringer Mannheim) for two hours at 64° C., and then boiled for 10 minutes. No further purification is performed.

III. Preparation of the Reagent Mixture

To a 500 ul microfuge tube (USA Scientific) is placed a reagent mixture containing 800 ng of each of the four synthetic oligonucleotide probes in 240 ul of 20 mM Tris-HCl pH 7.6; 10 mM MgAc; 25 mM KAc; 0.6 mM NAD; 10 mM DTT; 0.2 mM dATP; 0.2 mM dTTP; 400 units of heat stable ligase (Epicenter); 20 units of Taq polymerase (Perkin Elmer); and 1.75 ug human placenta DNA (Sigma).

The following control solutions are used:
40 ng/ul HeLa DNA (Negative Control).
40 ng/ul Human Placenta DNA (Negative Control).
40 ng/ul Ca Ski Cell DNA (Positive Control).
100 ng/ul No Target (Oligonucleotide Probes Only).

IV. Procedure

Thirty microliters of the reagent mixture is placed in each of seven 500 ul microfuge tubes. 1 ul of each test sample or control solution is added to each separate tube containing the reagent mixture. 25 ul of light mineral oil is added to each tube to cover the solution to prevent evaporation.

The tubes are arranged as follows:

| Tube | Contents |
| --- | --- |
| 1 | Biopsy #41 |
| 2 | Biopsy #63 |
| 3 | Biopsy #59 |
| 4 | Ca Ski DNA |
| 5 | HeLa DNA |
| 6 | Human Placenta DNA |
| 7 | No Target |

The tubes are incubated as follows:

94° C. for 3 minutes.

30–40 Cycles at:

90° C. for 1 minute.

50° C. for 2 minutes.

62° C. for 3 minutes.

4° C. until ready for analysis.

V. Detection

Method A. Sizing on a Gel.

The reaction products are separated by size using 12% nondenaturing polyacrylamide gels, followed by staining the gels with ethidium bromide.

Method B. Non-radioactive capture assay format (Fluorescein and Biotin).

Procedure:

1. The wells of a microtiter plate (Immulon II) are coated with 10 ug of egg white avidin (Precision Chemicals) in 100 ul of PBS and incubated overnight at 4° C.

2. The wells of the microtiter plate are washed two times with PBS/0.5% Tween (PBST). The wells are further coated by adding 100 ul of 2% BSA in PBS to each well for 30 min. at room temperature (RT). The blocking solution is decanted and the wells are washed 3 times with PBST.

3. Following incubation of the reaction tubes, the reaction mixture is adjusted, with gentle mixing, to a volume of 100 ul with PBS. 50 ul of the adjusted reaction mixture is transferred from each reaction tube to a separate blocked well on the microtiter plate. The mixtures in the microtiter wells are incubated for one hour at room temperature.

4. The reaction mixtures are decanted from the microtiter wells. The wells of the plate are washed five times with PBST. A rabbit anti-fluorescein alkaline-phosphate conjugated antibody (Biodesign) is diluted 1:100 in PBS. 100 ul of the conjugate is added to each well of the microtiter plate and incubated for one hour at room temperature.

5. The conjugate solution is decanted from the microtiter wells. The plate is washed five times with PBST. 100 ul of para-nitrophenylphospate (pNpp) substrate (1 mg/ml ) is added to each well of the microtiter plate and incubated for fifteen minutes at room temperature. 100 ul of 2N NaOH is added to each well of the microtiter plate. The optical density (O.D.) of each well is read at 405 nm.

IV. Results

1. The Ca Ski target titration experiment shows that after 40 cycles of amplification, 1 picogram (or approximately 180 copies) of Ca Ski DNA target can be produced and detected in a discernable band in an ethidium bromide stained 12% nondenaturing polyacrylamide gel.

Figure 2:
FIG. 2 shows the results of amplification, by the gap filling-ligation embodiment, of HPV16 DNA in clinical samples obtained by biopsy and detection by a non-radioactive capture assay. (Example 19).

2. The results of amplification using clinical samples as targets shows that all three 'Southern hybridization' typed HPV16 positive samples tested also give strong positive signals in the non-radioactive capture assay (FIG. 2) and strong bands in an ethidium bromide stained 12% nondenaturing polyacrylamide gel.

3. Titration of genomic cervical DNA targets obtained from a biopsy shows that approximately 10 picograms of DNA can be specifically produced with the HPV16 reagents after 40 cycles of amplification and detected in the direct capture color assay.

EXAMPLE 20

This example illustrates the gap filing-ligation embodiment to amplify and detect target DNA sequences of hepatitis B virus (HBV). Three sources of HBV DNA are used in this example. The first is a 3.2 Kb plasmid denoted "HBVp3.2." The second source is an immortalized cell line that contains seven copies of the HBV genome and is denoted "PLC." The third source is an immortalized cell line that contains one copy of the HBV genome and is denoted "Hep3B." The HBV target DNA sequence is the 734–791 region of the genome having the sequence:

5' CAGTTATATGGATGATGTGGTAT-TGGGGGCCAAGTCTGTACAGCATCT-TGAGTCCCTT 3'

3' GTCAATATACCTACTACACCATAAC-CCCCGGTTCAGACATGTCGTAGAACTCAGGGAA 5'

See SEQ ID NO's. 37–38.

The gaps formed when the respective oligonucleotide pairs are hybridized to each of the target sequences are underlined above.

In each of the complementary oligonucleotide pairs, there are 5' overhung bases. The 5' and 3' ends are protected with an amino linker arm, which is useful in non-radioactive labeling. The construction of the oligonucleotides is as follows:

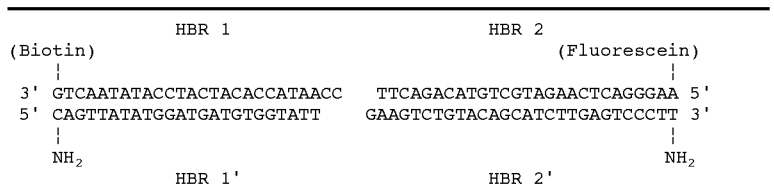

See SEQ ID NO's. 39–42 (HBR 2, HBR 1, HBR 1' and HRB 2' respectively).

When these oligonucleotide pairs are hybridized to the HBV target sequence, a gap exists between each pair as illustrated:

I. Procedure

Materials:

Each 30 ul aliquot of reaction mixture contains the following:

100 ng (0.4 uM) of each of the four synthetic oligonucleotide probes; Biotin-HBR-1, HBR-1'; Fluorescein-HBR-2, HBR-2'.

100 units of heat stable ligase (Epicenter).

5 units of Taq polymerase (Perkin Elmer).

in: 20 mM Tris-HCl pH 7.6, 10 mM MgAc, 25 mM KAc, 0.6 mM NAD, 10 mM DTT, 0.2 mM dGTP and 0.2 mM of dCTP, 0.1% Triton X-100.

Method I: Titration of the HBV samples.

30 ul of reaction mixture is added to each of 10 microfuge tubes (500 ul size).

To the first tube is added 1 ul of a sample (negative control) containing 100 ng of human placenta DNA in distilled water ($dH_2O$).

To each successive tube is added 2–5 ul of a serial dilution of HBVp3.2, PLC cell line, Hep3B or HBV transfected cell line DNA target sequences as follows:

| Tube | DNA Contents | |
|---|---|---|
| 1 | Control, no target | |
| 2 | HBVp3.2 | 40 pg |
| 3 | HBVp3.2 | 0.8 pg |
| 4 | HBVp3.2 | 0.16 pg |
| 5 | PLC | 200 ng |
| 6 | PLC | 20 ng |
| 7 | PLC | 2 ng |
| 8 | Hep3B | 200 ng |
| 9 | Hep3B | 20 ng |
| 10 | Hep3B | 2 ng |

Method II: Amplification of HBV samples for detection with a capture assay.

To each successive tube is added 1–2 ul of a sample of HBVp3.2, PLC cell line or Hep3B HBV DNA target sequences as follows:

| Tube | DNA Contents | |
|---|---|---|
| 1 | Control, no target (NT1) | |
| 2 | Control, no target (NT2) | |
| 3 | HBVp3.2 | 6.0 ng |
| 4 | PLC | 20.0 ng |
| 5 | Hep3B | 80.0 ng |

Each of the tubes is covered with 25 ul of light mineral oil to prevent evaporation.

The tubes are placed in a DNA Thermal Cycler (Perkin Elmer Model 4800).

The tubes are incubated as follows:

94° C. for 3 minutes.

30–40 Cycles at:

90° C. for 1 minute.

50° C. for 2 minutes.

62° C. for 3 minutes.

4° C. until ready for analysis.

After the cycling is completed, the contents of each tube is analysed either on a gel or in a capture assay.

Detection:

Method A. Sizing on a Gel.

The reaction products are separated by size using 12% nondenaturing polyacrylamide gels. 50 ul of dye solution containing 30% glycerol in water and 0.1% bromophenol blue is added to each of the six tubes in the first set.

Twenty microliters of solution from each tube is loaded on a 12% polyacrylamide gel using Tris-borate buffer (pH 8). Electrophoresis is carried out at 20 volts/cm for three hours, after which the gel is exposed to a Kodak X-OMAT AR film for three hours.

Method B. Non-radioactive capture assay format (Fluorescein and Biotin).

Procedure:

1. The wells of a microtiter plate (Immulon II) are coated with 10 ug of egg white avidin (Precision Chemicals) in 100 ul of PBS and incubated overnight at 4° C.

2. The wells of the microtiter plate are washed two times with PBS/0.5% Tween (PBST). The wells are further coated by adding 100 ul of 2% BSA in PBS to each well for 30 min. at room temperature (RT). The blocking solution is decanted and the wells are washed 3 times with PBST.

3. Following incubation of the reaction tubes, the reaction mixture is adjusted, with gentle mixing, to a volume of 100 ul with PBS. 50 ul of the adjusted reaction mixture is transferred from each reaction tube to a separate blocked well on the microtiter plate. The mixtures in the microtiter wells are incubated for one hour at room temperature.

4. The reaction mixtures are decanted from the microtiter wells. The wells of the plate are washed five times with PBST. A horse raddish peroxidase conjugated rabbit anti-fluorescein antibody (Biodesign) is diluted 1:10,000 in PBS. 100 ul of the conjugate is added to each well of the microtiter plate and incubated for one hour at room temperature.

5. The conjugate solution is decanted from the microtiter wells. The wells are washed five times with PBST. 100 ul of TMB and hydrogen peroxide (1:1 vol.) substrate solution is added to each well of the microtiter plate and incubated for thirty minutes at room temperature. 100 ul of $H_2SO_4$ is added to each well. The optical density (O.D.) of each well is read at 450 nm, using a microtiter plate reader. The results are shown in FIG. 4.

What is claimed is:

1. A process for detecting a specific nucleic acid target molecule in a sample by amplifying the nucleic acid target molecule, the process comprising the steps of:
    a) treating the sample with at least two oligonucleotides for each strand of the target molecule, under hybridizing conditions,
        i) wherein the oligonucleotides are selected so as to be sufficiently complementary to each strand of the target molecule to hybridize therewith under the hybridizing conditions; and
        ii) wherein a gap of one or more bases is present between two oligonucleotides when the two oligonucleotides are hybridized to a strand of the target molecule; and
        iii) wherein the oligonucleotides are selected so that the gaps between them will require less than all four types of bases to fill the gaps;
    b) filling the gaps formed in step (a) with one or more bases complementary to the base or bases in the gaps and joining the base or bases filling the gaps to each other and to both adjacent hybridized oligonucleotides, thereby forming a joined oligonucleotide product;
    c) treating the hybridized joined oligonucleotide product of step (b) under denaturing conditions to separate the joined oligonucleotide products from the target molecule to produce single-stranded molecules;
    d) treating the single-stranded molecules produced in step (c) with an excess of at least two oligonucleotide complement pairs, under hybridizing conditions,
        i) wherein each oligonucleotide complement pair comprises two oligonucleotides selected so as to be sufficiently complementary to each other, to each strand of the target molecule and to the joined oligonucleotide products to hybridize therewith under the hybridizing conditions; and
        ii) wherein gaps of one or more bases are present between the oligonucleotides when the oligonucleotides are hybridized to each strand of the target molecule; and
        iii) wherein the oligonucleotides are selected so that the gaps between them will require less than all four types of bases to fill the gaps;

e) filling in the gaps formed in step (d) with one or more bases complementary to the base or bases in the gaps and joining the bases filling the gaps to each other and to both adjacent hybridized oligonucleotides, thereby forming additional joined oligonucleotide products, resulting in the amplification of the target molecule; and f) detecting the joined oligonucleotide products.

2. The process of claim 1, further including step e') treating the hybridized oligonucleotides of step e) under denaturing conditions to separate the hybridized oligonucleotides and produce single-stranded molecules, wherein steps (d), (e) and (e') are repeated a desired number of times.

3. The process of claim 1, wherein the nucleic acid target molecule is double-stranded DNA and its strands are separated before or during step (a).

4. The process of claim 1, wherein the nucleic acid target molecule is single-stranded DNA.

5. The process of claim 1, wherein the nucleic acid target molecule is single-stranded RNA.

6. The process of claim 1, wherein the oligonucleotides are oligodeoxyribonucleotides.

7. The process of claim 1, wherein the oligonucleotide complement pairs are present as a molar excess in the range of $10^5$ to $10^{15}$ pairs per nucleic acid target molecule.

8. The process of claim 1, wherein the gaps are filled by a DNA polymerase and a DNA ligase.

9. The process of claim 8, wherein the DNA polymerase and the DNA ligase are immobilized on polymeric supports.

10. The process of claim 8, wherein the DNA polymerase is selected from the group consisting of *E. coli* DNA polymerase-I, Klenow fragments of *E. coli* DNA polymerase-I, T4 DNA polymerase, and reverse transcriptase and the DNA ligase is selected from the group consisting of *E. coli* DNA ligase and T4 DNA ligase.

11. The process of claim 8, wherein the DNA polymerase is heat stable.

12. The process of claim 8, wherein the DNA ligase is heat stable.

13. The process of claim 8, wherein the heat stable polymerase and ligase are isolated from a thermophilic bacteria.

14. The process of claim 1, wherein the oligonucleotides and/or deoxyribonucleic triphosphates are modified to be resistant to 3'→5' exonuclease activity.

15. A process for detecting a specific nucleic acid target molecule in a sample by amplifying the nucleic acid target molecule, the process comprising the steps of:

a) treating the sample with at least two oligonucleotides for each strand of the target molecule, under hybridizing conditions,
   i) wherein the oligonucleotides are selected so as to be sufficiently complementary to each strand of the target molecule to hybridize therewith under the hybridizing conditions; and
   ii) wherein a gap of more than one bases is present between two oligonucleotides when the two oligonucleotides are hybridized to a strand of the target molecule; and
   iii) wherein the oligonucleotides are selected so that the gaps between them will require less than all four types of bases to fill the gaps;

b) filling the gaps formed in step (a) with one or more bases complementary to the base or bases in the gaps and joining the base or bases filling the gaps to each other and to both adjacent hybridized oligonucleotides, thereby forming a joined oligonucleotide product;

c) treating the hybridized joined oligonucleotide product of step (b) under denaturing conditions to separate the joined oligonucleotide products from the target molecule to produce single-stranded molecules;

d) treating the single-stranded molecules produced in step (c) with an excess of at least two oligonucleotide complement pairs, under hybridizing conditions,
   i) wherein each oligonucleotide complement pair comprises two oligonucleotides selected so as to be sufficiently complementary to each other, to each strand of the target molecule and to the joined oligonucleotide products to hybridize therewith under the hybridizing conditions; and
   ii) wherein gaps of more than one bases are present between the oligonucleotides when the oligonucleotides are hybridized to each strand of the target molecule; and
   iii) wherein the oligonucleotides are selected so that the gaps between them will require less than all four types of bases to fill the gaps;

e) filling in the gaps formed in step (d) with one or more bases complementary to the base or bases in the gaps and joining the bases filling the gaps to each other and to both adjacent hybridized oligonucleotides, thereby forming additional joined oligonucleotide products, resulting in the amplification of the target molecule; and f) detecting the joined oligonucleotide products.

* * * * *

UNITED STATES PATENT AND TRADEMARK OFFICE
CERTIFICATE OF CORRECTION

PATENT NO. : 6,004,826
DATED : December 21, 1999
INVENTOR(S) : Segev

It is certified that error appears in the above-identified patent and that said Letters Patent are hereby corrected as shown below:

<u>In Column 9, line 10,</u>   now reads "T4-DNA polymerase. oligonucleotide.
should read --T4-DNA polymerase. Oligonucleotide.--;

<u>In Column 22, line 14,</u>   now reads "Jy=3'-y-P-GAGACCTTTcCAC..."
should read --Jy=3'-y-P-GAGACCTTTCCAC...--;

<u>In Column 22, line 23,</u>   now reads "(GUSCN)"
should read --(GuSCN)--;

<u>In Column 30, line 61,</u>   now reads "10 UCi"
should read --10 uCi--;

<u>In Column 34, line 43,</u>   now reads "capture color assay."
should read --capture color assay (Figure 3).--;

Signed and Sealed this

Twenty-fourth Day of April, 2001

Attest:

NICHOLAS P. GODICI

Attesting Officer      Acting Director of the United States Patent and Trademark Office